(12) United States Patent
Wennogle et al.

(10) Patent No.: US 10,398,698 B2
(45) Date of Patent: *Sep. 3, 2019

(54) USES

(71) Applicant: INTRA-CELLULAR THERAPIES, INC., New York, NY (US)

(72) Inventors: Lawrence P. Wennogle, Hillsborough, NJ (US); Robert Davis, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/709,258

(22) Filed: Sep. 19, 2017

(65) Prior Publication Data

US 2018/0000825 A1 Jan. 4, 2018
US 2018/0177782 A9 Jun. 28, 2018

Related U.S. Application Data

(63) Continuation of application No. 14/767,489, filed as application No. PCT/US2014/016741 on Feb. 17, 2014, now Pat. No. 9,801,882.

(60) Provisional application No. 61/765,804, filed on Feb. 17, 2013.

(51) Int. Cl.
*A61K 31/519* (2006.01)
*A61K 45/06* (2006.01)

(52) U.S. Cl.
CPC ............ *A61K 31/519* (2013.01); *A61K 45/06* (2013.01)

(58) Field of Classification Search
None
See application file for complete search history.

(56) References Cited

U.S. PATENT DOCUMENTS

| | | |
|---|---|---|
| 4,666,908 A | 5/1987 | Hamilton |
| 4,722,810 A | 2/1988 | Delaney et al. |
| 4,929,641 A | 5/1990 | Haslanger et al. |
| 5,202,328 A | 4/1993 | de Laszlo et al. |
| 5,217,996 A | 6/1993 | Ksander |
| 5,294,612 A | 3/1994 | Bacon et al. |
| 5,393,755 A | 2/1995 | Neustadt et al. |
| 5,824,683 A | 10/1998 | McKittrick et al. |
| 5,849,770 A | 12/1998 | Head et al. |
| 5,939,419 A | 8/1999 | Tulshian et al. |
| 5,962,492 A | 10/1999 | Warrellow et al. |
| 6,013,621 A | 1/2000 | Nishi et al. |
| 6,133,273 A | 10/2000 | Gilbert et al. |
| 6,221,335 B1 | 4/2001 | Foster |
| 6,235,742 B1 | 5/2001 | Bell et al. |
| 6,235,746 B1 | 5/2001 | Davis et al. |
| 6,316,444 B1 | 11/2001 | Hunt et al. |
| 6,334,997 B1 | 1/2002 | Foster et al. |
| 6,423,716 B1 | 7/2002 | Matsuno et al. |
| 6,440,710 B1 | 8/2002 | Keinan et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,603,008 B1 | 8/2003 | Ando et al. |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,157,451 B2 | 1/2007 | Atwal et al. |
| 7,517,990 B2 | 4/2009 | Ito et al. |
| 7,964,607 B2 | 6/2011 | Verhoest et al. |
| 8,273,750 B2 | 9/2012 | Li et al. |
| 8,273,751 B2 | 9/2012 | Li et al. |
| 8,513,244 B2 | 8/2013 | Gendron et al. |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 8,829,008 B2 | 9/2014 | Li et al. |
| 8,846,693 B2 | 9/2014 | Li et al. |
| 8,858,911 B2 | 10/2014 | Li et al. |
| 8,859,564 B2 | 10/2014 | Li et al. |
| 8,927,556 B2 | 1/2015 | Li et al. |
| 9,000,001 B2 | 4/2015 | Li et al. |
| 9,006,258 B2 | 4/2015 | Fienberg et al. |
| 9,073,936 B2 | 7/2015 | Li et al. |
| 9,157,906 B2 | 10/2015 | Greengard et al. |
| 9,198,924 B2 | 12/2015 | Mates et al. |
| 9,255,099 B2 | 2/2016 | Li et al. |
| 9,371,327 B2 | 6/2016 | Li et al. |
| 9,403,836 B2 | 8/2016 | Li |
| 9,434,730 B2 | 9/2016 | Li et al. |
| 9,468,637 B2 | 10/2016 | Fienberg et al. |
| 9,469,647 B2 | 10/2016 | Li et al. |
| 9,487,527 B2 | 11/2016 | Li et al. |
| 9,624,230 B2 | 4/2017 | Li et al. |
| 9,763,948 B2 | 9/2017 | Li et al. |
| 9,801,882 B2 | 10/2017 | Wennogle et al. |
| 9,884,872 B2 | 2/2018 | Li et al. |

(Continued)

FOREIGN PATENT DOCUMENTS

| | | |
|---|---|---|
| DE | 19931206 A1 | 1/2001 |
| DE | 10 2005 042 877 A1 | 3/2007 |

(Continued)

OTHER PUBLICATIONS

Adamo et al., "Molecular targets for PDE inhibitor-mediated improvement of cardiac dysfunction in the mdx mouse?", BMC Pharmacology, 2011, 11(Suppl 1):O20 (Abstract Only).

(Continued)

*Primary Examiner* — Heidi Reese
(74) *Attorney, Agent, or Firm* — Hoxie & Associates LLC

(57) ABSTRACT

The invention relates to the administration of inhibitors of phosphodiesterase 1 (PDE1) for the treatment of diseases or disorders characterized by disruption of or damage to various cGMP/PKG mediated pathways. In one embodiment the invention relates to inhibitors of phosphodiesterase 1 (PDE1) for treatment of cardiovascular disease and related disorders, e.g., congestive heart disease, atherosclerosis, myocardial infarction, and stroke.

16 Claims, No Drawings

(56) References Cited

U.S. PATENT DOCUMENTS

| | | |
|---|---|---|
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2003/0211040 A1 | 11/2003 | Greengard et al. |
| 2004/0087517 A1 | 5/2004 | Burnet et al. |
| 2004/0259792 A1 | 12/2004 | Palmer et al. |
| 2005/0075795 A1 | 4/2005 | Pandit |
| 2005/0113379 A1 | 5/2005 | Ge et al. |
| 2006/0041014 A1 | 2/2006 | Naylor et al. |
| 2006/0252790 A1 | 11/2006 | Allen et al. |
| 2007/0082929 A1 | 4/2007 | Gant et al. |
| 2007/0197695 A1 | 8/2007 | Potyen et al. |
| 2008/0096870 A1 | 4/2008 | Martynyuk et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0273754 A1 | 10/2010 | Li |
| 2010/0323997 A1 | 12/2010 | Fienberg et al. |
| 2011/0190373 A1 | 8/2011 | Yan et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0070443 A1 | 3/2012 | Movsesian |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li |
| 2012/0238589 A1 | 9/2012 | Li |
| 2013/0018063 A1 | 1/2013 | Li et al. |
| 2013/0085123 A1 | 4/2013 | Li et al. |
| 2013/0149309 A1 | 6/2013 | Greengard et al. |
| 2013/0239234 A1 | 9/2013 | Greengard et al. |
| 2013/0324565 A1 | 12/2013 | Li et al. |
| 2013/0330365 A1 | 12/2013 | Hughes et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2014/0275131 A1 | 9/2014 | Li et al. |
| 2014/0315868 A1 | 10/2014 | Li et al. |
| 2014/0357606 A1 | 12/2014 | Li et al. |
| 2015/0038474 A1 | 2/2015 | Li et al. |
| 2015/0072965 A1 | 3/2015 | Li et al. |
| 2015/0080357 A1 | 3/2015 | Li et al. |
| 2015/0119370 A1 | 4/2015 | Li et al. |
| 2015/0197524 A1 | 7/2015 | Li et al. |
| 2015/0197528 A1 | 7/2015 | Li et al. |
| 2015/0353556 A1 | 12/2015 | Li et al. |
| 2015/0374699 A1 | 12/2015 | Wennogle et al. |
| 2016/0031895 A1 | 2/2016 | Li et al. |
| 2016/0038494 A1 | 2/2016 | Wennogle et al. |
| 2016/0039835 A1 | 2/2016 | Li et al. |
| 2016/0083390 A1 | 3/2016 | Li et al. |
| 2017/0197974 A1 | 7/2017 | Li et al. |
| 2017/0226117 A1 | 8/2017 | Li et al. |

FOREIGN PATENT DOCUMENTS

| | | |
|---|---|---|
| EP | 0 063 381 A1 | 10/1982 |
| EP | 0 095 289 A2 | 11/1983 |
| EP | 0136883 A2 | 4/1985 |
| EP | 0 201 188 A2 | 12/1986 |
| EP | A 0274234 A2 | 7/1988 |
| EP | 0358398 A1 | 3/1990 |
| EP | 0509442 A1 | 10/1992 |
| EP | 0519738 A1 | 12/1992 |
| EP | 0599444 A1 | 6/1994 |
| EP | 0 636 626 A1 | 2/1995 |
| EP | 0690070 A1 | 1/1996 |
| EP | 0733642 A1 | 9/1996 |
| EP | 0830863 A1 | 3/1998 |
| EP | 0 911 333 A1 | 4/1999 |
| EP | 1097719 A1 | 5/2001 |
| JP | 53031694 A | 3/1978 |
| KR | 10-1991-0006866 | 9/1991 |
| WO | WO 91/09840 | 7/1991 |
| WO | WO 91/19717 | 12/1991 |
| WO | WO 93/09101 | 5/1993 |
| WO | WO 94/15908 | 7/1994 |
| WO | WO 94/19351 | 9/1994 |
| WO | WO 96/14293 | 5/1996 |
| WO | WO 98/46606 | 10/1998 |
| WO | WO 98/52568 | 11/1998 |
| WO | WO 01/27113 | 4/2001 |
| WO | WO 02/074312 | 9/2002 |
| WO | WO 03/002567 | 1/2003 |
| WO | WO 03/020702 | 3/2003 |
| WO | WO 03/020724 | 3/2003 |
| WO | WO 03/042216 | 5/2003 |
| WO | WO 2006/133261 | 12/2006 |
| WO | WO 2007/143568 | 12/2007 |
| WO | WO 2007/143705 | 12/2007 |
| WO | WO 2008/063505 | 5/2008 |
| WO | WO 2008/070095 | 6/2008 |
| WO | WO 2009/073210 | 6/2009 |
| WO | WO 2009/075784 | 6/2009 |
| WO | WO 2009/137465 | 11/2009 |
| WO | WO 2010/065147 | 6/2010 |
| WO | WO 2010/065148 | 6/2010 |
| WO | WO 2010/065149 | 6/2010 |
| WO | WO 2010/065151 | 6/2010 |
| WO | WO 2010/065152 | 6/2010 |
| WO | WO 2010/065153 | 6/2010 |
| WO | WO 2010/065617 | 6/2010 |
| WO | WO 2010/098839 | 9/2010 |
| WO | WO 2011/016861 | 2/2011 |
| WO | WO 2011/043816 | 4/2011 |
| WO | WO 2011/133224 | 10/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/171016 | 12/2012 |
| WO | WO 2013/192556 | 12/2013 |
| WO | WO 2014/127331 | 8/2014 |
| WO | WO 2014/151409 | 9/2014 |
| WO | WO 2016/022893 | 2/2016 |

OTHER PUBLICATIONS

Ahn, H. et al., "Potent Tetracyclic Guanine Inhibitors of PDE1 and PDE5 Cyclic Guanosine Monophosphate Phosphodiesterases with Oral Antihypertensive Activity," Journal of Medicinal Chemistry, 1997, 40 (14), 2196-2210.

Al-Afaleq, E. et al., "Heterocyclic o-Aminonitriles: Preparation of Pyrazolo[3,4-d]-pyrimidines with Modification of the Substituents at the 1-Position," Molecules, 2001, 6, 621-638.

"Anxiety," [retrieved on May 14, 2008]. Retrieved online via Internet, URL: http://www.nlm.nih.gov/medlineplus/anxiety.html, 5 pages.

Aswar, M. et al., "Anti-Cataleptic Activity of Various Extracts of *Ocimum sanctum*," International Journal of Pharmaceutical Research and Development, 2010, 2 (6), 7 pages.

"Autism," [retrieved on May 14, 2008]. Retrieved online via Internet, URL: http://www.nlm.nih.gov/medlineplus/autism.html, 6 pages.

Banker, Gilbert S. et al., Eds., Modern Pharmaceutics, Third Edition, Marcel Dekker Inc., New York, 1996.

Bastia, E. et al., "Effect of $A_1$ and $A_{2A}$ Adenosine Receptor Ligands in Mouse Acute Models of Pain," Neuroscience Letters, 2002, 328, 241-244.

Bender, A. et al., "Cyclic Nucleotide Phosphodiesterases: Molecular Regulation to Clinical Use," Pharmacological Reviews, 2006, 58 (3), 488-520.

(56) References Cited

OTHER PUBLICATIONS

Blokland, A. et al., "PDE Inhibition and Cognition Enhancement," 2012, 22 (4), 349-354 (abstract only).
Boyd, K. et al., "Dopamine Receptor Signaling and Current and Future Antipsychotic Drugs" in Current Antipsychotics, Handbook of Experimental Pharmacology, 212, Gross, G. et al., Eds., doi:10.1007/978-3-642-25761-2_3, Springer-Verlag, Berlin, 2012, pp. 53-86.
Burnouf, C. et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors," Journal of Medicinal Chemistry, 2000, 43 (25), 4850-4867.
Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.
Chebib, M. et al., "1-Phenylpyrazolo[3,4-d]pyrimidines; Structure-Activity Relationships for C6 Substituents at $A_1$ and $A_{2A}$ Adenosine Receptors," Bioorganic & Medicinal Chemistry, 2000, 8, 2581-2590.
Chen, M. et al., "Effects of Bimatoprost 0.03% on Ocular Hemodynamics in Normal Tension Glaucoma," Journal of Ocular Pharmacology and Therapeutics, 2006, 22 (3), 188-193.
Chermat, R. et al., "Adaptation of the Tail Suspension Test to the Rat," Journal de Pharmacologie (Paris), 1986, 17 (3), 348-350.
Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.
Dewald, H. et al., "Synthesis and Potential Antipsychotic Activity of 1H-Imidazo[1,2-c]pyrazolo[3,4-e]pyrimidines," Journal of Medicinal Chemistry, 1988, 31, 454-461.
Ehrman, L. et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, 2006, 5 (7), 540-551.
English Abstract of DE19931206, date of publication of application: Jan. 11, 2001, 2 pages, obtained through E-Spacenet, date accessed: Oct. 6, 2017.
English Abstract of DE102005042877, date of publication of application: Mar. 22, 2007, 1 page, obtained through E-Spacenet, date accessed: Nov. 15, 2016.
Ennaceur, A. et al., "A New One-Trial Test for Neurobiological Studies of Memory in Rats. 1:Behavioral Data," Behavioural Brain Research, 1998, 31, 47-59.
Fienberg, A. et al., "DARPP-32: Regulator of the Efficacy of Dopaminergic Neurotransmission," Science, 1998, 281, 838-842.
Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.
Gelbin, M. et al., "Ketene-S,N-acetals as Synthons for Heterocycles, New Synthesis of Pyrimidinones," Journal Für Praktische Chemie, 1987, 329 (5), 753-766.
Ghorab, M.M. et al, Synthesis, anticancer and radioprotective activities of some new pyrazolo[3,4-d]pyrimidines containing amino acid moieties, Arzneimittel Forschung, 2009, vol. 59, No. 2, pp. 96-103.
Giachini et al., "CHBPR: Decreased cGMP level contributes to increased contraction in arteries from hypertensive rats: role of PDE1", Hypertension, 2011, 57(3): 655-663.
Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.
Greengard, P. et al., "Beyond the Dopamine Receptor: The DARPP-32/Protein Phosphatase-1 Cascade," Neuron, 1999, 23, 435-447.
Gulyas, B. et al., "PET studies on the brain uptake and regional distribution of [11C]vinpocetine in human subjects," Acta Neurologica Scandinavica, 2002, 106: 325-332.
Hall et al., "Autoradiographic evaluation of [11C]vinpocetine Binding in the Human Postmortem Brain," Acta Biologica Hungarica, 2002, 53(1-2): 59-66.
Han, P. et al., "The Calcium/Calmodulin-dependent Phosphodiesterase PDE1C Down-regulates Glucose-induced Insulin Secretion," The Journal of Biological Chemistry, 1999, 274 (32), 22337-22344.
Hulley, P. et al., "Cyclic AMP Promotes the Survival of Dopaminergic Neurons in vitro and Protects Them from the Toxic Effects of MPP+," Journal of Neural Transmission [Supplemental], 1995, 46, 217-228.
International Search Report for International Application No. PCT/US2014/016741, prepared by the International Searching Authority, dated May 14, 2014, 3 pages.
International Search Report for International Application No. PCT/US2015/044164, prepared by the International Searching Authority, dated Oct. 29, 2015, 3 pages.
Japanese Patent Office, Patent Abstracts of Japan, Abstract for JP 53031694 A, Date of publication of application Mar. 25, 1978, 1 page.
Jiang, M. et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," Journal of Organic Chemistry, 2005, 70, 2824-2827.
Kakkar, R. et al., "Inhibition of Bovine Brain Calmodulin-Dependent Cyclic Nucleotide Phosphodiesterase Isozymes by Deprenyl," Life Sciences, 1996, 59 (21), 337-341.
Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.
Kakkar, R. et al. "Calmodulin-dependent Cyclic Nucleotide Phosphodiesterase (PDE1)," CMLS Cellular and Molecular Life Sciences, 1999, 55 (8-9), 1164-1186.
Kakkar et al., "Calmodulin-dependent cyclic nucleotide phosphodiesterase in an experimental rat model of cardiac ischemia-reperfusion." Can J Physiol Pharmacol, 2002, 80(1):59-66 (Abstract Only).
Kim et al., "Upregulation of Phosphodiesterase 1A1 Expression Is Associated With the Development of Nitrate Tolerance." Circulation, 2001, 104(19):2338-43.
Klaissle, P. et al., "Physical Activity and Environmental Enrichment Regulate the Generation of Neural Precursors in the Adult Mouse Substantia Nigra in a Dopamine-dependent Manner," BMC Neuroscience, 2012, 13, 132, doi:10.1186/1471-2202-13-132, 15 pages.
Kleppisch, T., "Phosphodiesterases in the Central Nervous System" in cGMP: Generators, Effectors and Therapuetic Implications, Handbook of Experimental Pharmacology, 191, Schmidt, H. et al., Eds., Springer-Verlag, Berlin, 2009, pp. 71-92.
Laddha, S. et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, 2009, 17 (19), 6796-6802.
Lundqvist, T. et al., "Exploitation of Structural and Regulatory Diversity in Glutamate Racemases," Nature, 2007, 447, 817-822.
Lourenco et al, "Characterization of R-[11C]rolipram for PET imaging of phosphodiesterase-4; in vivo binding, metabolism, and dosimetry studies in rats," Nuclear Medicine and Biology, 2001, 28: 347-358.
Mani, S. et al., "Requirement for DARPP-32 in Progesterone Facilitated Sexual Receptivity in Female Rats and Mice," Science, 2000, 287, 1053-1056.
Medina, A., "Therapeutic Utility of Phosphodiesterase Type 1 Inhibitors in Neurological Conditions," Frontiers in Neuroscience, 2011, 5, 21, 6 pages.
Miller et al., "Role of Ca2+/calmodulin-stimulated cyclic nucleotide phosphodiesterase 1 in mediating cardiomyocyte hypertrophy." Circ Res 2009, 105(10):956-64.

(56) References Cited

OTHER PUBLICATIONS

Miller et al., "Cyclic nucleotide phosphodiesterase 1A: a key regulator of cardiac fibroblast activation and extracellular matrix remodeling in the heart," Basic Res Cardiol., 2011, 106(6): 1023-1039.
Mokni et al., "Concerted Regulation of cGMP and cAMP Phosphodiesterases in Early Cardiac Hypertrophy Induced by Angiotensin II," PLoS One., 2010 5(12):e14227, 15 pages.
Murray, F., et al., "Expression and activity of cAMP phosphodiesterase isoforms in pulmonary artery smooth muscle cells from patients with pulmonary hypertension: role for PDE1," Am. J. Physiol. Lunr:1 Cell Mol. Physiol. 2007, 292, pp. L294-L303.
Murray, T. et al., "LY503430, A Novel α-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.
Noguchi, M. et al., "A Facile Preparation of 7-(Substituted Amino-)-6H-pyrrolo[3,4-d]-pyrimidine Derivatives," Bulletin of the Chemical Society of Japan, 1989, 62 (9), 3043-3045.
Pardo, C. et al., "Synthesis of 1-(p-Nitrobenzyl)Azoles and 1-(p-Nitrobenzyl)Benzazoles," OPPI Briefs, 2000, 32 (4), 385-390.
Park, E, et al., "Traumatic Brain Injury: Can the Consequences Be Stopped?" CMAJ, 2008, 178 (9), 1163-1170.
Patani et al., "Bioisosterism: A Rational Approach in Drug Design", Chem. Rev. 1996, 96, 3147-3176.
Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.
Porsolt, R. et al., "Depression: A New Animal Model Sensitive to Antidepressant Treatments," Nature, 1977, 266, 730-732.
Poulsen, S. et al., "High-Pressure Synthesis of Enantiomerically Pure C-6 Substituted Pyrazolo[3,4-d]pyrimidines," Biorganic & Medicinal Chemistry Letters, 2001, 11, 191-193.
Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.
Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.
Rybalkin, S. et al., "Cyclic GMP Phosphodiesterases and Regulation of Smooth Muscle Function," Circulation Research, 2003, 93, 280-291.
Rybalkin et al., "Cyclic Nucleotide Phosphodiesterase 1C Promotes Human Arterial Smooth Muscle Cell Proliferation," Circulation Research, 2002, 90(2):151-7.
Schmidt, C., "Phosphodiesterase Inhibitors as Potential Cognition Enhancing Agents," Current Topics in Medicinal Chemistry, 2010, 10 (2), 222-230.
Sharma, R. et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from *Dictyostelium*," Cancer Research, 2004, 64, 2568-2571.
Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.

Silva, "Advances in Prodrug Design," Mini-Reviews in Medicinal Chemistry, 2005, 5:893-914.
Takimoto, E., "Controlling Myocyte cGMP: Phosphodiesterase 1 Joins the Fray," Circ Res., 2009, 105(10):931-933.
Turko, I. et al., "Inhibition of Cyclic GMP-Binding Cyclic GMP-Specific Phosphodiesterase (Type 5) by Sildenafil and Related Compounds," Molecular Pharmacology, 1999, 56, 124-130.
Ungerstedt, U. et al., "Quantitative Recording of Rotational Behavior in Rats After 6-Hydroxy-dopamine Lesions of the Nigrostriatal Dopamine System," Brain Research, 1970, 24, 485-493.
Ungerstedt, U., "Stereotaxic Mapping of the Monoamine Pathways in the Rat Brain," Acta Physiologica Scandinavica, Supplementum 367, 1971, 1-48.
Vas, A. et al. "Clinical and non-clinical investigations using positron emission tomography, near infrared spectroscopy and transcranial Doppler methods on the neuroprotective drug vinpocetine: A summary of evidences," Journal of the Neurological Sciences, 2002, 203-204: 259-262.
Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.
Wallis et al., "Tissue distribution of phosphodiesterase families and the effects of sildenafil on tissue cyclic nucleotides, platelet function, and the contractile responses of trabeculae carneae and aortic rings in vitro.", Am J Cardiol., 1999, 83(5A): 3C-12C.
Wermuth, CG, ed., "Molecular Variations based on isosteric replacements" The Practice of Chemistry, Technomics, Inc., Aug. 1998, vol. 1, Section 13, pp. 235-271, Japanese Translated Version.
Wolff, Burger's Medicinal Chemistry and Drug Discovery, Fifth Edition, vol. I: Principles and Practice, John Wiley & Sons, New York, 1995, 975-977.
Xia et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.
Youdim et al., "The Path from Anti Parkinson Drug Selegiline and Rasagiline to Multi-functional Neuroprotective Anti Alzheimer Drugs Ladostigil and M30," Current Alzheimer Research, 2006, 3, 541-550.
Zhang et al., "Phosphodiesterases and cardiac cGMP: evolving roles and controversies," Trends in Pharmacological Sciences, 2011, 32(6): 360-365.
Hashimoto, T. et al. "Acute Enhancement of Cardiac Function by Phosphodiesterase Type 1 Inhibition: A Translational Study in the Dog and Rabbit," Circulation, 2018, 138(18):1974-1987.
Leroy, J. et al. "Inhibit a Phosphodiesterase to Treat Heart Failure? This is the One," Circulation, 2018, 138:2003-2006.
Bender et al., "Selective up-regulation of PDE1B2 upon monocyte-to-macrophage differentiation," PNAS, 2005, 102(2):497-502.
English Abstract of EP0063381, date of publication of application: Oct. 27, 1982, 1 page, obtained through E-Spacenet, date accessed: Mar. 20, 2018.
Evgenov et al., "Inhibition of phosphodiesterase 1 augments the pulmonary vasodilator response to inhaled nitric oxide in awake lambs with acute pulmonary hypertension," Am J Physiol Lung Cell Mol Physiol, 2006, 290:L723-L729.
Kotera et al., "Recent progress in cyclic nucleotide phosphodiesterase research: isozymes, functions, and inhibitors," Folia Pharmacol. Jpn., 2005, 126(2):121-127.
Schermuly et al., "Phosphodiesterase 1 Upregulation in Pulmonary Arterial Hypertension," Circulation, 2007, 115:2331-2339.
Snyder, G.L. et al., "Preclinical Profile of ITI-214, an Inhibitor of Phosphodiesterase 1, for Enhancement of Memory Performance in Rats," Psychopharmacology, 2016, 233, 3113-3124, DOI: 10.1007/s00213-016-4346-2.
"The Diagnosis and Management of Duchenne Muscular-Dystrophy: A Guide for Families," Treat-NMD, First Issue, 2011, [retrieved on Mar. 6, 2018], Retrieved from the Internet: <URL:: http://www.treat-nmd.eu/downloads/file/standardsofcare/dmd/japan/DMDweb03_02pass.pdf>.
Willerson et al., "Inflammation as a Cardiovascular Risk Factor," Circulation, 2004, 109: II-2-II-10.

USES

CROSS-REFERENCE TO RELATED APPLICATIONS

This application is a continuation of U.S. application Ser. No. 14/767,489, filed on Aug. 12, 2015, which is a National Phase Application filed under 35 U.S.C. 371 of International Application No. PCT/US2014/016741, filed on Feb. 17, 2014, which claims priority to U.S. Provisional Application No. 61/765,804, filed on Feb. 17, 2013, the contents of each of which are herein incorporated by reference in their entirety.

FIELD OF THE INVENTION

The field relates to the administration of inhibitors of phosphodiesterase 1 (PDE1) for the treatment of diseases or disorders characterized by disruption of or damage to certain cGMP/PKG mediated pathways (e.g., in cardiac tissue). The field further relates to inhibitors of phosphodiesterase 1 (PDE1) for treatment of cardiovascular disease and related disorders, e.g., congestive heart disease, atherosclerosis, myocardial infarction, and stroke.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), which are activated by the $Ca^{2+}$-calmodulin and have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation.

Although PDE1B is primarily expressed in the central nervous system, it may be detected in the heart. PDE1C is expressed in olfactory epithelium, cerebellar granule cells, striatum, heart, and vascular smooth muscle. Specifically, the major PDE activity in the human cardiac ventricle is PDE1. And PDE1 has been shown to promote human arterial smooth muscle cell proliferation. By virtue of its modulation of cGMP in the monocyte, PDE1 has potential as a hypertrophy regulator. (Circ Res. 2009 Nov. 6; 105(10): 931.) Generally, there is a high abundance of PDE1 isoforms in: cardiac myocytes, vascular endothelial smooth muscle, fibroblast and motor neurons.

Cyclic nucleotide phosphodiesterases downregulate intracellular cAMP and cGMP signaling by hydrolyzing these cyclic nucleotides to their respective inactive 5'-monophosphates (5'AMP and 5'GMP). cGMP is a central intracellular second-messenger regulating numerous cellular functions. In the cardiac myocyte, cGMP mediates effects of nitric oxide and atrial natriuretic peptide, whereas its counterpart, cAMP, mediates catecholamine signaling. Each cyclic nucleotide has a corresponding primary targeted protein kinase, PKA for cAMP, and PKG for cGMP. PKA stimulation is associated with enhanced contractility and can stimulate growth, whereas PKG acts as a brake in the heart, capable of countering cAMP-PKA-contractile stimulation and inhibiting hypertrophy. Importantly, the duration and magnitude of these signaling cascades are determined not only by generation of cyclic nucleotides, but also by their hydrolysis catalyzed by phosphodiesterases (PDEs). PDE regulation is quite potent—often suppressing an acute rise in a given cyclic nucleotide back to baseline within seconds to minutes. It is also compartmentalized within the cell, so that specific targeted proteins can be regulated by the same "generic" cyclic nucleotide.

Heart disease is typically a chronic and progressive illness that kills more than 2.4 million Americans each year. There are approximately 500,000 new cases of heart failure per year, with an estimated 5 million patients in the United States alone having this disease. Early intervention is likely to be most effective in preserving cardiac function. It would be most desirable to prevent as well to reverse the morphological, cellular, and molecular remodeling that is associated with heart disease. Some of the most important indicators of cardiac risk are age, hereditary factors, weight, smoking, blood pressure, exercise history, and diabetes. Other indicators of cardiac risk include the subject's lipid profile, which is typically assayed using a blood test, or any other biomarker associated with heart disease or hypertension. Other methods for assaying cardiac risk include, but are not limited to, an EKG stress test, thallium stress test, EKG, CT scan, echocardiogram, magnetic resonance imaging study, non-invasive and invasive arteriogram, and cardiac catheterization.

Pulmonary hypertension (PH or PHT) is an increase in blood pressure in the pulmonary artery, pulmonary vein, and/or pulmonary capillaries. It is a very serious condition, potentially leading to shortness of breath, dizziness, fainting, decreased exercise tolerance, heart failure, pulmonary edema, and death. It can be one of five different groups, classified by the World Health Organization as follows:

WHO Group I Pulmonary arterial hypertension (PAH)
a. Idiopathic (IPAH)
b. Familial (FPAH)
c. Associated with other diseases (APAH): collagen vascular disease (e.g. scleroderma), congenital shunts between the systemic and pulmonary circulation, portal hypertension, HIV infection, drugs, toxins, or other diseases or disorder.
d. Associated with venous or capillary disease Pulmonary arterial hypertension involves the vasoconstriction or tightening of blood vessels connected to and within the lungs. This makes it harder for the heart to pump blood through the lungs, much as it is harder to make water flow through a narrow pipe as opposed to a wide one. Over time, the affected blood vessels become both stiffer and thicker, in a process known as fibrosis. This further increases the blood pressure within the lungs and impairs their blood flow. In addition, the increased workload of the heart causes thickening and enlargement of the right ventricle, making the heart less able to pump blood through the lungs, causing right heart failure. As the blood flowing through the lungs decreases, the left side of the heart receives less blood. This blood may also carry less oxygen than normal. Therefore it becomes more and more difficult for the left side of the heart to pump to supply sufficient oxygen to the rest of the body, especially during physical activity.

WHO Group II—Pulmonary hypertension associated with left heart disease a. Atrial or ventricular disease
b. Valvular disease (e.g. mitral stenosis)

In pulmonary venous hypertension (WHO Group II) there may not be any obstruction to blood flow in the lungs. Instead, the left heart fails to pump blood efficiently out of the heart into the body, leading to pooling of blood in veins leading from the lungs to the left heart (congestive heart failure or CHF). This causes pulmonary edema and pleural effusions. The fluid build-up and damage to the lungs may also lead to hypoxia and consequent vasoconstriction of the pulmonary arteries, so that the pathology may come to resemble that of Group 1 or III.

WHO Group III—Pulmonary hypertension associated with lung diseases and/or hypoxemia a. Chronic obstructive pulmonary disease (COPD), interstitial lung disease (ILD) b. Sleep-disordered breathing, alveolar hypoventilation c. Chronic exposure to high altitude d. Developmental lung abnormalities In hypoxic pulmonary hypertension (WHO Group II I), the low levels of oxygen may cause vasoconstriction or tightening of pulmonary arteries. This leads to a similar pathophysiology as pulmonary arterial hypertension.

WHO Group IV—Pulmonary hypertension due to chronic thrombotic and/or embolic disease a. Pulmonary embolism in the proximal or distal pulmonary arteries b. Embolization of other matter, such as tumor cells or parasites In chronic thromboembolic pulmonary hypertension (WHO Group IV), the blood vessels are blocked or narrowed with blood clots. Again, this leads to a similar pathophysiology as pulmonary arterial hypertension.

WHO Group V—Miscellaneous

Treatment of pulmonary hypertension has proven very difficult.

Antihypertensive drugs that work by dilating the peripheral arteries are frequently ineffective on the pulmonary vasculature. For example, calcium channel blockers are effective in only about 5% of patients with IPAH. Left ventricular function can often be improved by the use of diuretics, beta blockers, ACE inhibitors, etc., or by repair/replacement of the mitral valve or aortic valve. Where there is pulmonary arterial hypertension, treatment is more challenging, and may include lifestyle changes, digoxin, diuretics, oral anticoagulants, and oxygen therapy are conventional, but not highly effective. Newer drugs targeting the pulmonary arteries, include endothelin receptor antagonists (e.g., bosentan, sitaxentan, ambrisentan), phosphodiesterase type 5 inhibitors (e.g., sildenafil, tadalafil), prostacyclin derivatives (e.g., epoprostenol, treprostenil, iloprost, beroprost), and soluble guanylate cyclase (sGC) activators (e.g., cinaciguat and riociguat). Surgical approaches to PAH include atrial septostomy to create a communication between the right and left atria, thereby relieving pressure on the right side of the heart, but at the cost of lower oxygen levels in blood (hypoxia); lung transplantation; and pulmonary thromboendarterectomy (PTE) to remove large clots along with the lining of the pulmonary artery. Heart failure and acute myocardial infarction are common and serious conditions frequently associated with thrombosis and/or plaque build-up in the coronary arteries.

Cardiovascular disease or dysfunction may also be associated with diseases or disorders typically thought of as affecting skeletal muscle. One such disease is Duchenne muscular dystrophy (DMD), which is a disorder that primarily affects skeletal muscle development but can also result in cardiac dysfunction and cardiomyopathy. DMD is a recessive X-linked form of muscular dystrophy, affecting around 1 in 3,600 boys, which results in muscle degeneration and eventual death. The disorder is caused by a mutation in the dystrophin gene, located on the human X chromosome, which codes for the protein dystrophin, an important structural component within muscle tissue that provides structural stability to the dystroglycan complex (DGC) of the cell membrane. While both sexes can carry the mutation, females rarely exhibit signs of the disease.

Patients with DMD lack expression of the protein dystrophin as a result of mutations in the X-linked dystrophin gene. Additionally, the loss of dystrophin leads to severe skeletal muscle pathologies as well as cardiomyopathy, which manifests as congestive heart failure and arrhythmias. The absence of a functional dystrophin protein is believed to lead to reduced expression and mis-localization of dystrophin-associated proteins including neuronal nitric oxide (NO) synthase. Disruption of nNOS signaling may result in muscle fatigue and unopposed sympathetic vasoconstriction during exercise, thereby increasing contraction-induced damage in dystrophin-deficient muscles. The loss of normal nNOS signaling during exercise is central to the vascular dysfunction proposed to be an important pathogenic mechanism in DMD.

Currently, there is a largely unmet need for an effective way of treating cardiovascular disease and disorders (e.g. congestive heart disease), and diseases and disorders which may result in cardiac dysfunction or cardiomyopathy (e.g., Duchenne Muscular Dystrophy). Improved therapeutic compositions and methods for the treatment of cardiac conditions and dysfunction are urgently required.

SUMMARY OF THE INVENTION

PDE1A and PDE1C are believed to be abundantly expressed in cardiac, vascular, and lung tissues. Moreover, PDE1 is also believed to be up-regulated in chronic disease conditions such as atherosclerosis, cardiac pressure-load stress and heart failure, as well as in response to long-term exposure to nitrates. Without being bound by theory, it is believed that the compounds of the present invention are able to modulate cGMP/PKG mediated pathways. Consequently, the PDE1 inhibitors disclosed herein are believed to have significant modulatory activity (e.g., enhancement of cGMP) in those areas of the body where PDE1 isoforms are predominately located: e.g., cardiac, vascular, and lung tissue. PDE1 inhibitors may have relatively little impact on resting function, but rather maintain the ability to potently modulate acute contractile tone in cells stimulated by vasoactive agonists.

For example, it is believed that PDE1 may modulate acute contractile tone in cells that are activated by hypertrophic stimuli. Consequently, without being bound by theory, it is believed that in one embodiment that the application or administration of the PDE1 inhibitors disclosed herein could work to prevent hypertrophic responses and possibly reverse any existing tissue hypertrophy.

Without being bound by theory, in one embodiment it is believed that the selective PDE1 inhibitors, e.g., Compounds of Formula I, II, III, IV, V, VI, VII, VIII, IX, X, and XI described herein, may be involved in regulating cGMP/PKG involvement in cardiac hypertrophy. Previous studies have demonstrated that intracellular Ca2+/CaM-dependent signaling promotes maladaptive hypertrophic gene expression in cardiomyocytes through various effectors such as the protein phosphatase calcineurin, Ca2+/CaM-dependent kinase II (CaMKII). Without being bound by any theory, Endogenous cGMP/PKG-dependent signaling may be able to negatively regulate cardiac hypertrophy, by suppressing Gq/11 activation and normalizing Ca2+ signaling. Ca2+/CaM, by activating PDEIA, may decrease cGMP levels and PKG activity. In turn, this process may lead to potentiated cardiomyocyte hypertrophy. Additionally, upregulation of PDE1A expression upon neurohumoral or biomechanical stress during cardiac hypertrophy may further enhance PDE1A activity and attenuates cGMP/PKG signaling. Accordingly, without being bound by any theory, it is believed that inhibition of PDE1A, for example, could reverse or prevent the attenuation of cGMP/PKG signaling. Therefore, administration of a preferred PDE1 inhibitor as described herein could provide a potential means to regulate cardiac hypertrophy, and by extension provide a treatment for various cardiovascular diseases and disorders.

Accordingly, in one embodiment, the invention provides a new method of treatment or prophylaxis of cardiovascular disease and disorders (e.g., atherosclerosis, pulmonary arterial hypertension, myocardial infarction) that may be ameliorated by administration of a specific inhibitor of phosphodiedsterase type I (e.g., PDE1 inhibitor, e.g., a PDE1A or PDE1C inhibitor) (e.g., a PDE1 inhibitor of Formula I, II, III, IV, V, VI, VII, VIII, IX, X, and/or XI as herein described).

In one embodiment the cardiovascular disease or disorder may selected from the group consisting of: hypertension, congestive heart failure, angina, stroke, essential hypertension, pulmonary hypertension, secondary pulmonary hypertension, isolated systolic hypertension, hypertension associated with diabetes, hypertension associated with atherosclerosis, renovascular hypertension, congestive heart failure, angina, stroke. In certain embodiments, the cardiovascular disease or disorder to be treated may also relate to impaired cGMP/PKG-dependent signaling.

In another embodiment the PDE1 inhibitor (e.g., a PDE1 inhibitor of Formula I, II, III, IV, V, VI, VII, VIII, IX, X, and/or XI as herein described) may be administered in combination with an angiotensin II receptor antagonist. Examples of angiotensin II receptor antagonists for use with the invention include candesartan, eprosartan, irbesartan, losartan, olmesartan, olmnesartan medoxomil, saralasin, telmisartan and valsartan.

The invention also provides a new method of treatment or prophylaxis of cardiovascular disease or disorder that is associated with a muscular dystrophy (e.g, Duchenne muscular dystrophy). As previously noted, DMD is caused by the absence of a functional dystrophin protein, which in turn leads to reduced expression and mis-localization of dystrophin-associated proteins; which can include neuronal nitric oxide (NO) synthase. Disruption of nNOS signaling may result in muscle fatigue and unopposed sympathetic vasoconstriction during exercise, thereby increasing contraction-induced damage in dystrophin-deficient muscles. Without being bound by theory, the loss of normal nNOS signaling during exercise may be central to the vascular dysfunction proposed to be an important pathogenic mechanism in DMD. Without being bound by theory, it is contemplated that by inhibiting phosphodiesterases (e.g. PDE1A, PDE1C), (e.g., administering or using a PDE1 inhibitor of Formula I, II, III, IV, V, VI, VII, VIII, IX, X, and/or XI as herein described) that at least one mechanism of the compounds described herein may be to circumvent defective nNOS signaling in dystrophic skeletal and/or cardiac muscle; thereby potentially improving cardiac outcomes in, at least, DMD patients.

In one particular embodiment, the invention provides a novel method of treatment or prophylaxis for cardiac dysfunction associated with Duchenne muscular dystrophy that may be ameliorated by administration of a phosphodiesterase type I (PDE1 inhibitor, e.g., a PDE1 inhibitor of Formula I, II, III, IV, V, VI, VII, VIII, IX, X, and/or XI as herein described) as described herein.

In another embodiment, the PDE1 inhibitor is administered to a patient with a type of muscular dystrophy which may be selected from the group consisting of: Becker, limb-girdle, myotonic, and Emery-Dreifuss muscular dystrophy.

In one embodiment, the invention provides for the treatment of cardiovascular disease or disorder which may be associated with impaired cGMP signaling (e.g., cGMP/PKG signaling), wherein the disease or disorder may be selected from the group consisting of: angina, stroke, essential hypertension, pulmonary hypertension, secondary hypertension, isolated systolic hypertension, hypertension associated with diabetes, hypertension associated with atherosclerosis, renovascular hypertension, congestive heart failure, angina, stroke, hypertension, fibrosis, an inflammatory disease or disorder, cardiac hypertrophy, and an connective tissue disease or disorder (e.g., Marfan Syndrome).

DETAILED DESCRIPTION OF THE INVENTION

Compounds for Use in the Methods of the Invention

In one embodiment, the PDE1 inhibitors for use in the methods of treatment and prophylaxis described herein are optionally substituted 4,5,7,8-tetrahydro-2H-imidazo[1,2-a] pyrrolo[3,4-e]pyrimidine or 4,5,7,8,9-pentahydro-2H-pyrimido[1,2-a]pyrrolo[3,4-e]pyrimidine, e.g., a Compound of Formula II, e.g., II-A or II-B:

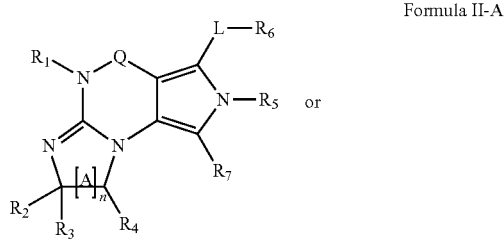

Formula II-A

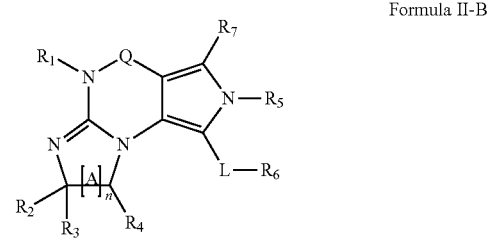

Formula II-B wherein
(i) Q is C(=O), C(=S), C(=N(R$_{20}$)) or CH$_2$;
(ii) L is a single bond, —N(H)—, —CH$_2$—, —S—, —S(O)— or —S(O$_2$)—;
(iii) R$_1$ is H or C$_{1-4}$ alkyl (e.g., methyl);
(iv) R$_4$ is H or C$_{1-6}$ alkyl (e.g., methyl or isopropyl) and R$_2$ and R$_3$ are, independently,
H
C$_{1-6}$alkyl (e.g., methyl, isopropyl) optionally substituted with halo or hydroxy (e.g., R$_2$ and R$_3$ are both methyl, or R$_2$ is H and R$_3$ is methyl, ethyl, isopropyl or hydroxyethyl),
aryl,
heteroaryl,
(optionally hetero)arylalkoxy,
(optionally hetero)arylC$_{1-6}$alkyl; or
R$_2$ and R$_3$ together form a 3- to 6-membered ring;
or
R$_2$ is H and R$_3$ and R$_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
or
(v) $R_5$ is
a) -D-E-F, wherein:
D is $C_{1-4}$alkylene (e.g., methylene, ethylene or prop-2-yn-1-ylene);
E is a single bond, $C_{2-4}$alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl), halo (e.g., F, Br, Cl),
halo$C_{1-4}$alkyl (e.g., trifluoromethyl),
—C(O)—$R_{15}$,
—N($R_{16}$)($R_{17}$), or
$C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more halo (e.g., F, Cl or Br), $C_{1-4}$alkyl (e.g., methyl), halo$C_{1-4}$alkyl (e.g., trifluoromethyl), $C_{1-4}$alkoxy (e.g., methoxy), hydroxy, $C_{1-4}$carboxy, or an additional aryl or heteroaryl (e.g., biphenyl or pyridylphenyl),
for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$alkyl (e.g., 5-methylpyrid-2-yl), or F is aryl, e.g., phenyl, substituted with one or more halo (e.g., 4-fluorophenyl) or F is a $C_{3-7}$heterocycloalkyl (e.g., pyrrolidinyl) optionally substituted with a $C_{1-6}$alkyl (e.g., 1-methylpyrrolidin-3-yl); or
b) a substituted heteroarylalkyl, e.g., substituted with halo$C_{1-4}$alkyl;
c) attached to the nitrogen on the pyrrolo portion of Formula II-A or II-B and is a moiety of Formula A

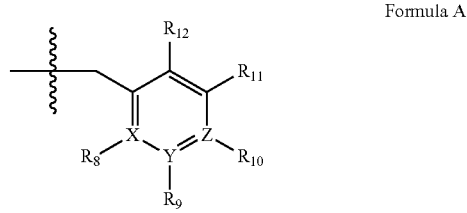

Formula A wherein X, Y and Z are, independently, N or C, and $R_8$, $R_9$, $R_{11}$ and $R_{12}$ are independently H or halogen (e.g., Cl or F), and $R_{10}$ is
halogen,
$C_{1-4}$alkyl,
halo$C_{1-4}$alkyl (e.g., triflouromethyl)
$C_{1-4}$alkoxy (e.g. methoxy),
$C_{3-7}$cycloalkyl,
hetero$C_{3-7}$cycloalkyl (e.g., pyrrolidinyl or piperidinyl),
$C_{1-4}$haloalkyl (e.g., triflouromethyl),
aryl (e.g., phenyl),
heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently, optionally substituted with one or more $C_{1-4}$ alkyl (e.g., methyl), halogen (e.g., chloro or fluoro), halo$C_{1-4}$alkyl (e.g., trifluoromethyl), hydroxy, $C_{1-4}$carboxy, —SH or an additional aryl, heteroaryl (e.g., biphenyl or pyridylphenyl) or $C_{3-8}$cycloalkyl,
preferably $R_{10}$ is phenyl, pyridyl, piperidinyl or pyrrolidinyl optionally substituted with the substituents previously defined, e.g. optionally substituted with halo or alkyl
provided that when X, Y, or Z is nitrogen, $R_8$, $R_9$, or $R_{10}$, respectively, is not present;
(vi) $R_6$ is
H,
$C_{1-4}$alkyl (e.g., methyl, ethyl, n-propyl, isobutyl),
$C_{3-7}$cycloalkyl (e.g., cyclopentyl or cyclohexyl),
hetero$C_{3-7}$cycloalkyl (e.g., pyrrolidinyl, piperidinyl, morpholinyl),
aryl (e.g., phenyl),
heteroaryl (e.g., pyrid-4-yl),
aryl$C_{1-4}$alkyl (e.g., benzyl),
arylamino (e.g., phenylamino),
heteroarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$),
wherein the aryl and heteroaryl are optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, or an additional aryl, heteroaryl (e.g., biphenyl or pyridylphenyl) or $C_{3-8}$ cycloalkyl;
(vii) $R_7$ is H, $C_{1-6}$alkyl (e.g., methyl or ethyl), halogen (e.g., Cl), —N($R_{18}$)($R_{19}$), hydroxy or $C_{1-6}$alkoxy;
(viii) n=0 or 1;
(ix) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{14}$ can form a bridge with $R_2$ or $R_4$;
(x) $R_{15}$ is $C_{1-4}$alkyl, halo$C_{1-4}$alkyl, —OH or —O$C_{1-4}$alkyl (e.g., —OCH$_3$)
(xi) $R_{16}$ and $R_{17}$ are independently H or $C_{1-4}$alkyl;
(xii) $R_{18}$ and $R_{19}$ are independently
H,
$C_{1-4}$alky (e.g., methyl, ethyl, n-propyl, isobutyl),
$C_{3-8}$cycloalky (e.g., cyclohexyl or cyclopenyl),
hetero$C_3$cycloalky (e.g., pyrrolidinyl, piperidinyl, morpholinyl),
aryl (e.g., phenyl) or
heteroaryl (e.g., pyridyl),
wherein said aryl and heteroaryl are optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl), C$_{1-4}$alkyl (e.g., methyl),
haloC$_{1-4}$alkyl (e.g., trifluoromethyl),
C$_{1-4}$carboxy, or
an additional aryl, heteroaryl (e.g., biphenyl or pyridylphenyl) or C$_{3-8}$cycloalkyl;
(xiii) R$_{20}$ is H, C$_{1-4}$alkyl or C$_{3-7}$cycloalkyl;
in free or salt form.

In another embodiment, the PDE1 inhibitors for use in the methods of treatment and prophylaxis described herein are Compound of Formula I, e.g. Formula I-A and I-B:

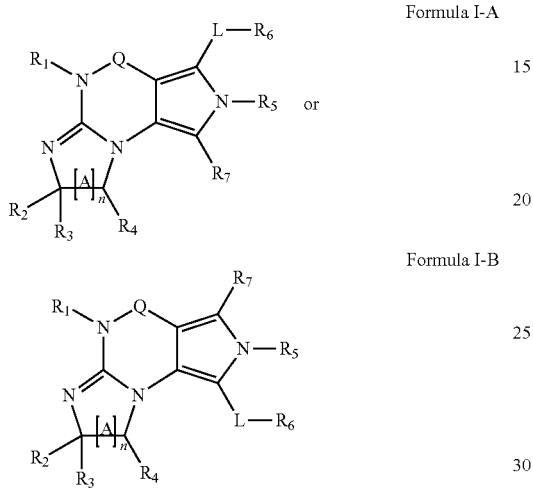

Formula I-A

Formula I-B wherein
(i) Q is C(=O), C(=S), C(=N(R$_{20}$)) or CH$_2$;
(ii) L is a single bond, —N(H)—, —CH$_2$—, —S—, —S(O)— or S(O$_2$)—;
(iii) R$_1$ is H or C$_{1-4}$ alkyl (e.g., methyl);
(iv) R$_4$ is H or C$_{1-6}$ alkyl (e.g., methyl or isopropyl) and R$_2$ and R$_3$ are, independently,
H or C$_{1-6}$alkyl (e.g., methyl, isopropyl) optionally substituted with halo or hydroxy (e.g., R$_2$ and R$_3$ are both methyl, or R$_2$ is H and R$_3$ is methyl, ethyl, isopropyl or hydroxyethyl),
aryl,
heteroaryl,
(optionally hetero)arylalkoxy, or
(optionally hetero)arylC$_{1-6}$alkyl;
or
R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
(v) R$_5$ is
a) -D-E-F, wherein:
D is C$_{1-4}$alkylene (e.g., methylene, ethylene or prop-2-yn-1-ylene);
E is a single bond, C$_{2-4}$alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl),
halo (e.g., F, Br, Cl),
haloC$_{1-4}$alkyl (e.g., trifluoromethyl),
—C(O)—R$_{15}$,
—N(R$_{16}$)(R$_{17}$), or
C$_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more halo (e.g., F, Cl or Br), C$_{1-4}$alkyl (e.g., methyl), haloC$_{1-4}$alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$alkyl (e.g., 5-trifluoromethylpyrid-2-yl) or C$_{1-4}$alkyl (e.g., 5-methylpyrid-2-yl), or F is aryl, e.g., phenyl, substituted with one or more halo (e.g., 4-fluorophenyl) or F is a C$_{3-7}$ heterocycloalkyl (e.g., pyrrolidinyl) optionally substituted with a C$_{1-6}$alkyl (e.g., 1-methylpyrrolidin-3-yl); or
b) a substituted heteroarylalkyl, e.g., substituted with haloalkyl;
c) attached to the nitrogen on the pyrrolo portion of Formula I-A or I-B and is a moiety of Formula A

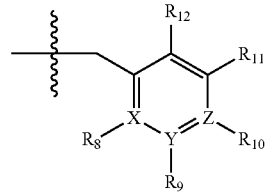

Formula A wherein X, Y and Z are, independently, N or C, and R$_8$, R$_9$, R$_{11}$ and R$_{12}$ are independently H or halogen (e.g., Cl or F), and R$_{10}$ is
halogen,
C$_{1-4}$alkyl,
C$_{3-7}$cycloalkyl,
C$_{1-4}$haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, R$_8$, R$_9$, or R$_{10}$, respectively, is not present;
(vi) R$_6$ is
H,
C$_{1-4}$alkyl,
C$_{3-7}$cycloalkyl (e.g., cyclopentyl),
aryl (e.g., phenyl),
heteroaryl (e.g., pyrid-4-yl),
arylC$_{1-4}$alkyl (e.g., benzyl),
arylamino (e.g., phenylamino),
heteroarylamino,
N,N-diC$_{1-4}$alkylamino,
N,N-diarylamino, N-aryl-N-(arylC$_{1-4}$alkyl)amino (e.g., N-phenyl-N-(1,1'-biphen-4-ylmethyl)amino), or

—N(R$_{18}$)(R$_{19}$);

wherein the aryl or heteroaryl is optionally substituted with one or more halo (e.g., F, Cl), hydroxy or C$_{1-6}$alkoxy;

(vii) R$_7$ is H, C$_{1-6}$alkyl, halogen (e.g., Cl), —N(R$_{18}$)(R$_{19}$);

(viii) n=0 or 1;

(ix) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy or (optionally hetero)arylC$_{1-4}$alkyl;

(x) R$_{15}$ is C$_{1-4}$alkyl, haloC$_{1-4}$alkyl, —OH or —OC$_{1-4}$alkyl (e.g., —OCH$_3$)

(xi) R$_{16}$ and R$_{17}$ are independently H or C$_{1-4}$alkyl;

(xii) R$_{18}$ and R$_{19}$ are independently H, C$_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)

(xiii) R$_{20}$ is H, C$_{1-4}$alkyl or C$_{3-7}$cycloalkyl;

in free or salt form.

1.1 any of the preceding formulae wherein the compounds inhibit phosphodiesterase-mediated (e.g., PDE1-mediated, especially PDE1B-mediated) hydrolysis of cGMP, e.g., with an IC$_{50}$ of less than 1 μM, preferably less than 750 nM, more preferably less than 500 nM, more preferably less than 50 nM in an immobilized-metal affinity particle reagent PDE assay, in free or salt form.

The invention further provides optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, in free or salt form, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazol o[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., a Compound of Formula III:

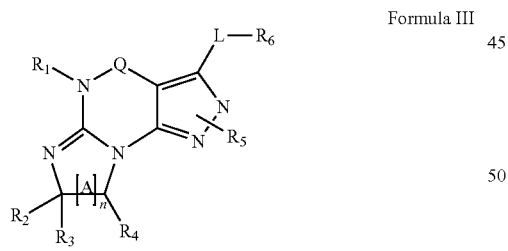

Formula III wherein (xiv) Q is C(=S), C(=N(R$_{20}$)) or CH$_2$;

(xv) L is a single bond, —N(H)—, —CH$_2$—;

(xvi) R$_1$ is H or C$_{1-4}$ alkyl (e.g., methyl or ethyl);

(xvii) R$_4$ is H or C$_{1-6}$ alkyl (e.g., methyl, isopropyl) and R$_2$ and R$_3$ are, independently:

H or C$_{1-6}$alkyl (e.g., methyl or isopropyl) optionally substituted with halo or hydroxy (e.g., R$_2$ and R$_3$ are both methyl, or R$_2$ is H and R$_3$ is methyl, ethyl, isopropyl or hydroxyethyl), aryl, heteroaryl, (optionally hetero)arylalkoxy, (optionally hetero)arylC$_{1-6}$alkyl, or R$_2$ and R$_3$ together form a 3- to 6-membered ring;

or

R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);

(xviii) R$_5$ is d) -D-E-F, wherein:

D is C$_{1-4}$alkylene (e.g., methylene, ethylene or prop-2-yn-1-ylene);

E is a single bond, C$_{2-4}$alkynylene (e.g., —C≡C—), arylene (e.g., phenylene) or heteroarylene (e.g., pyridylene);

F is

H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), haloC$_{1-4}$alkyl (e.g., trifluoromethyl),

—C(O)—R$_{15}$,

—N(R$_{16}$)(R$_{17}$),

—S(O)$_2$R$_{21}$ or

C$_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);

wherein D, E and F are independently and optionally substituted with one or more:

halo (e.g., F, Cl or Br),

C$_{1-4}$alkyl (e.g., methyl), haloC$_{1-4}$alkyl (e.g., trifluoromethyl),

C$_{1-4}$alkoxy) or

C$_{1-4}$alkyl (e.g., 5-methylpyrid-2-yl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), or F is aryl, e.g., phenyl, substituted with one or more halo (e.g., 4-fluorophenyl)

or F is a C$_{3-7}$heterocycloalkyl (e.g., pyrrolidinyl) optionally substituted with a C$_1$ 6alkyl (e.g., 1-methylpyrrolidin-3-yl);

or e) a substituted heteroarylalkyl, e.g., substituted with haloalkyl;

f) attached to one of the nitrogens on the pyrazolo portion of Formula III and is a moiety of Formula A

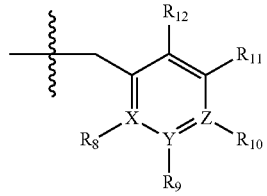

Formula A wherein X, Y and Z are, independently, N or C, and R$_8$, R$_9$, R$_{11}$ and R$_{12}$ are independently H or halogen (e.g., Cl or F), and R$_{10}$ is:

halogen,

C$_{1-4}$alkyl,

C$_{3-7}$cycloalkyl, hetC$_{3-7}$cycloalkyl (e.g., pyrrolidinyl or piperidinyl),
C$_{1-4}$haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently and optionally substituted with one or more halo (e.g., F or Cl), C$_{1-4}$alkyl, C$_{1-4}$alkoxy, C$_{1-4}$haloalkyl (e.g., trifluoromethyl), —SH;
preferably R$_{10}$ is phenyl, pyridyl, piperidinyl or pyrrolidinyl optionally substituted with the substituents previously defined, e.g. optionally substituted with halo or alkyl
provided that when X, Y, or Z is nitrogen, R$_8$, R$_9$, or R$_{10}$, respectively, is not present;
(xix) R$_6$ is
H,
C$_{1-4}$alkyl,
C$_{3-7}$cycloalkyl (e.g., cyclopentyl),
aryl (e.g., phenyl),
heteroaryl (e.g., pyridyl, for example, pyrid-4-yl),
arylC$_{1-4}$alkyl (e.g., benzyl),
arylamino (e.g., phenylamino),
heterarylamino,
N,N-diC$_{1-4}$alkylamino,
N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$);
wherein the aryl or heteroaryl is optionally substituted with one or more halo (e.g., F, Cl), hydroxy, C$_{1-6}$alkyl, C$_{1-6}$alkoxy, C$_{3-8}$cycloalkyl, for example, R$_6$ is 4-hydroxyphenyl or 4-fluorophenyl,
(xx) n=0 or 1;
(xxi) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy, (optionally hetero)arylC$_{1-4}$alkyl or R$_{13}$ or R$_{14}$ can form a bridge with R$_2$ or R$_4$;
(xxii) R$_{15}$ is C$_{1-4}$alkyl, haloC$_{1-4}$alkyl, —OH or —OC$_{1-4}$alkyl (e.g., —OCH$_3$)
(xxiii) R$_{16}$ and R$_{17}$ are independently H or C$_{1-4}$alkyl;
(xxiv) R$_{18}$ and R$_{19}$ are independently
H,
C$_{1-4}$alky,
C$_{3-8}$cycloalkyl,
heteroC$_{3-8}$cycloalkyl,
aryl (e.g., phenyl), or
heteroaryl,
wherein said aryl or heteroaryl is optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
C$_{1-6}$alkyl,
haloC$_{1-6}$alkyl,
C$_{1-6}$alkoxy,
aryl,
heteroaryl, or
C$_{3-8}$cycloalkyl;
(xxv) R$_{20}$ is H, C$_{1-4}$alkyl (e.g., methyl) or C$_{3-7}$cycloalkyl,
(xxvi) R$_{21}$ is C$_{1-6}$alkyl;
in free or salt form.

In yet another embodiment, the invention also provides a Compound of Formula IV:

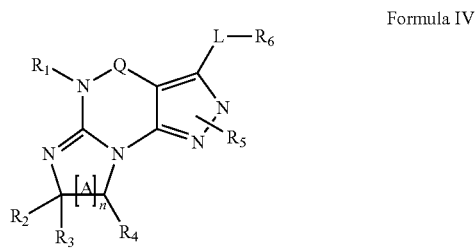

Formula IV wherein
(i) Q is C(=S), C(=N(R$_{20}$)) or CH$_2$;
(ii) L is a single bond, —N(H)—, —CH$_2$—;
(iii) R$_1$ is H or C$_{1-4}$ alkyl (e.g., methyl or ethyl);
(iv) R$_4$ is H or C$_{1-6}$ alkyl (e.g., methyl, isopropyl) and R$_2$ and R$_3$ are, independently, H or C$_{1-6}$alkyl (e.g., methyl or isopropyl) optionally substituted with halo or hydroxy (e.g., R$_2$ and R$_3$ are both methyl, or R$_2$ is H and R$_3$ is methyl, ethyl, isopropyl or hydroxyethyl), aryl, heteroaryl, (optionally hetero)arylalkoxy, or (optionally hetero)arylC$_{1-6}$alkyl;
or
R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
(v) R$_5$ is
a) -D-E-F, wherein:
D is C$_{1-4}$alkylene (e.g., methylene, ethylene or prop-2-yn-1-ylene);
E is a single bond, C$_{2-4}$alkynylene (e.g., —C≡C—), arylene (e.g., phenylene) or heteroarylene (e.g., pyridylene);
F is H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), haloC$_{1-4}$alkyl (e.g., trifluoromethyl), —C(O)—R$_{15}$, —N(R$_{16}$)(R$_{17}$), —S(O)$_2$R$_{21}$ or C$_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more:
halo (e.g., F, Cl or Br),
C$_{1-4}$alkyl (e.g., methyl),
haloC$_{1-4}$alkyl (e.g., trifluoromethyl),
for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$alkyl (e.g., 5-trifluoromethylpyrid-2-yl) or C$_{1-4}$alkyl (e.g., 5-methylpyrid-2-yl),
or F is aryl, e.g., phenyl, substituted with one or more halo (e.g., 4-fluorophenyl)

or F is a $C_{3-7}$heterocycloalkyl (e.g., pyrrolidinyl) optionally substituted with a $C_{1-6}$alkyl (e.g., 1-methylpyrrolidin-3-yl);
or
b) a substituted heteroarylalkyl, e.g., substituted with haloalkyl;
c) attached to one of the nitrogens on the pyrazolo portion of Formula IV and is a moiety of Formula A

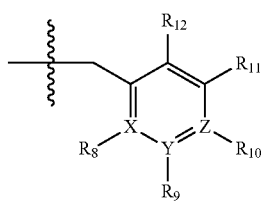

Formula A wherein X, Y and Z are, independently, N or C, and $R_8$, $R_9$, $R_{11}$ and $R_{12}$ are independently H or halogen (e.g., Cl or F), and $R_{10}$ is:
halogen,
$C_{1-4}$alkyl,
$C_{3-7}$cycloalkyl,
$C_{1-4}$haloalkyl (e.g., trifluoromethyl),
aryl (e.g., phenyl),
heteroaryl (e.g., pyridyl (for example pyrid-2-yl), or
thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, $R_8$, $R_9$, or $R_{10}$, respectively, is not present;
(vi) $R_6$ is
H,
$C_{1-4}$alkyl,
$C_{3-7}$cycloalkyl (e.g., cyclopentyl),
aryl (e.g., phenyl),
heteroaryl (e.g., pyridyl, for example, pyrid-4-yl),
aryl$C_{1-4}$alkyl (e.g., benzyl),
arylamino (e.g., phenylamino),
hetarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$);
wherein the aryl or heteroaryl is optionally substituted with one or more halo (e.g., F, Cl), hydroxy or $C_{1-6}$alkoxy, for example, $R_6$ is 4-hydroxyphenyl or 4-fluorophenyl,
(vii) n=0 or 1;
(viii) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy or (optionally hetero)aryl$C_{1-4}$alkyl;
(ix) $R_{15}$ is $C_{1-4}$alkyl, halo$C_{1-4}$alkyl, —OH or —O$C_{1-4}$alkyl (e.g., —OCH$_3$)
(x) $R_{16}$ and $R_{17}$ are independently H or $C_{1-4}$alkyl;
(xi) $R_{18}$ and $R_{19}$ are independently H, $C_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
(xii) $R_{20}$ is H, $C_{1-4}$alkyl (e.g., methyl) or $C_{3-7}$cycloalkyl,
(xiii) $R_{21}$ is $C_{1-6}$alkyl;
in free or salt form.

In still yet another embodiment, the invention provides that the PDE1 inhibitors for use in the methods of treatment and prophylaxis which are described herein are selected from any of the Applicant's own publications: US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, and WO 2011/153138, the entire contents of each of which are incorporated herein by reference in their entireties.

In yet another embodiment the invention provides that the PDE1 inhibitors for use in the methods of treatment and prophylaxis described herein are compounds of Formula V:

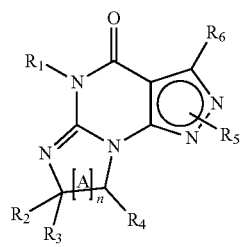

Formula V wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl or
$R_5$ is attached to one of the nitrogens on the pyrazolo portion of Formula V and is a moiety of Formula A

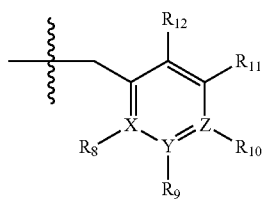

Formula A wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and (v) n=0 or 1;

(vi) when n=1, A is —C($R_{13}R_{14}$)—
wherein $R_{13}$ and $R_{14}$, are, independently, H or $C_{1-4}$ alkyl, aryl, heteroaryl,
(optionally hetero)arylalkoxy or (optionally hetero)arylalkyl;

in free, salt or prodrug form, including its enantiomers, diastereoisomers and racemates.

In one embodiment the invention provides that the PDE1 inhibitors for use in the methods of treatment and prophylaxis described herein are compounds of Formula VI:

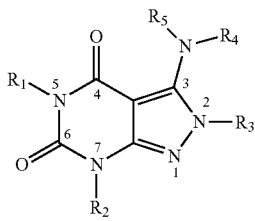

Formula VI wherein:

(i) $R_1$ is H or alkyl;

(ii) $R_2$ is H, alkyl, cycloalkyl, haloalkyl, alkylaminoalkyl, hydroxyalkyl, arylalkyl, heteroarylalkyl, or alkoxyarylalkyl;

(iii) $R_3$ is heteroarylmethyl or formula A

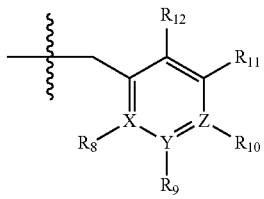

Formula A wherein X, Y and Z are, independently, N or C, and $R_8$, $R_9$, $R_{11}$ and $R_{12}$ are independently H or halogen; and $R_{10}$ is halogen, alkyl, cycloalkyl, haloalkyl, aryl, heteroaryl, alkyl sulfonyl, arylcarbonyl, heteroarylcarbonyl, alkoxycarbonyl, or aminocarbonyl;

(iv) $R_4$ is aryl or heteroaryl; and (v) $R_5$ is H, alkyl, cycloalkyl, heteroaryl, aryl, p-benzylaryl;

provided that when X, Y or X is nitrogen, $R_8$, $R_9$ or $R_{10}$, respectively, is not present; wherein "alk" or "alkyl" refers to $C_{1-6}$ alkyl and "cycloalkyl" refers to $C_{3-6}$ cycloalkyl, in free, salt or physiologically hydrolysable and acceptable ester prodrug form.

In one embodiment the invention provides that the PDE1 inhibitors for use in the methods of treatment and prophylaxis described herein are compounds of Formula VII:

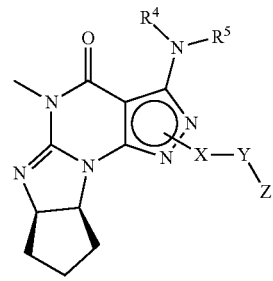

Formula VII (i) X is $C_{1-6}$alkylene (e.g., methylene, ethylene or prop-2-yn-1-ylene);

(ii) Y is a single bond, alkynylene (e.g., —C≡C—), arylene (e.g., phenylene) or heteroarylene (e.g., pyridylene);

(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—$R^1$, N($R^2$)($R^3$), or $C_{3-7}$cycloalkyl optionally containing at least one atom selected from a group consisting of N or O (e.g., cyclopentyl, cyclohexyl, tetrahydro-2H-pyran-4-yl, or morpholinyl);

(iv) $R^1$ is $C_{1-6}$alkyl, halo$C_{1-6}$alkyl, —OH or —O$C_{1-6}$alkyl (e.g., —OCH$_3$);

(v) $R^2$ and $R^3$ are independently H or $C_{1-6}$alkyl;

(vi) $R^4$ and $R^5$ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;

(vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl), in free, salt or prodrug form.

In one embodiment the invention provides that the PDE1 inhibitors for use in the methods of treatment and prophylaxis described herein are compounds of Formula VIII:

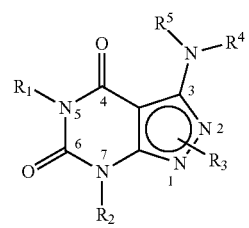

Formula VIII wherein (i) $R_1$ is H or $C_{1-6}$alkyl;

(ii) $R_2$ is
H,
$C_{1-6}$alkyl,
$C_{3-8}$cycloalkyl optionally substituted with one or more amino, $C_{3-8}$heterocycloalkyl optionally substituted with $C_{1-6}$alkyl, $C_{3-8}$cycloalkyl-$C_{1-6}$alkyl, $C_{1-6}$haloalkyl, $C_{0-6}$alkylamino$C_{0-6}$alkyl, hydroxy$C_{1-6}$alkyl, aryl$C_{0-6}$alkyl, heteroarylalkyl, $C_{1-6}$alkoxyaryl$C_{1-6}$alkyl, or -G-J wherein:
G is a single bond or, alkylene;
J is cycloalkyl or heterocycloalkyl optionally substituted with alkyl;

(iii) $R_3$ is
a) -D-E-F wherein
1. D is single bond, $C_{1-6}$alkylene or aryl$C_{1-6}$alkylene;
2. E is a $C_{1-6}$alkylene, arylene, $C_{1-6}$alkylarylene, amino$C_{1-6}$alkylene- or amino; and
3. F is hetero$C_{3-8}$cycloalkyl optionally substituted with $C_{1-6}$alkyl;

(iv) $R_4$ is aryl optionally substituted with one or more halo, hydroxy or $C_{1-6}$alkoxy; heteroaryl; or hetero$C_{3-6}$cycloalkyl; and (v) $R_5$ is H, $C_{1-6}$alkyl, $C_{3-8}$cycloalkyl, heteroaryl, aryl or p-benzylaryl;

wherein "alk", "alkyl", "haloalkyl" or "alkoxy" refers to $C_{1-6}$ alkyl and "cycloalkyl" refers to $C_{3-8}$cycloalkyl;

in free or salt form.

In one embodiment the invention provides that the PDE1 inhibitors for use in the methods of treatment and prophylaxis described herein are compounds of Formula IX:

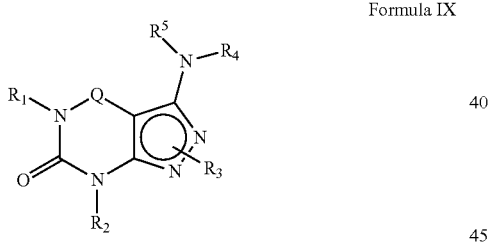

Formula IX wherein
(i) Q is —C(=S)—, —C(=N($R_6$))— or —C($R_{14}$)($R_{15}$)—;
(ii) $R_1$ is H or $C_{1-6}$alkyl (e.g., methyl or ethyl);
(iii) $R_2$ is
H,
$C_{1-6}$alkyl (e.g., isopropyl, isobutyl, 2-methylbutyl or 2,2-dimethylpropyl) wherein said alkyl group is optionally substituted with one or more halo (e.g., fluoro) or hydroxy (e.g., hydroxy$C_{1-6}$alkyl, for example 1-hydroxyprop-2-yl or 3-hydroxy-2-methylpropyl),
halo$C_{1-6}$alkyl (e.g., trifluoromethyl or 2,2,2-trifluoroethyl),
N($R_{14}$)($R_{15}$)—$C_{1-6}$alkyl (e.g., 2-(dimethylamino)ethyl or 2-aminopropyl),
aryl$C_{0-6}$alkyl (e.g., phenyl or benzyl), wherein said aryl is optionally substituted with one or more $C_{1-6}$alkoxy, for example, $C_{1-6}$alkoxyaryl$C_{0-6}$alkyl (e.g., 4-methoxybenzyl), heteroaryl$C_{0-6}$alkyl (e.g., pyridinylmethyl), wherein said heteroaryl is optionally substituted with one or more $C_{1-6}$alkoxy (e.g., $C_{1-6}$alkoxyheteroaryl$C_{1-6}$alkyl);

-G-J wherein G is a single bond or $C_{1-6}$alkylene (e.g., methylene) and J is $C_{3-8}$cycloalkyl or hetero$C_{3-8}$cycloalkyl (e.g., oxetan-2-yl, pyrrolidin-3-yl, pyrrolidin-2-yl) wherein the cycloalkyl and heterocycloalkyl group are optionally substituted with one or more $C_{1-6}$alkyl or amino, for example,
—$C_{0-4}$alkyl-$C_{3-8}$cycloalkyl (e.g., —$C_{0-4}$alkyl-cyclopentyl, —$C_{0-4}$alkyl-cyclohexyl or —$C_{0-4}$alkyl-cyclopropyl), wherein said cycloalkyl is optionally substituted with one or more $C_{1-6}$alkyl or amino (for example, 2-aminocyclopentyl or 2-aminocyclohexyl),
—$C_{0-4}$alkyl-$C_{3-8}$heterocycloalkyl (e.g., —$C_{0-4}$alkyl-pyrrolidinyl, for example, —$C_{0-4}$alkylpyrrolidin-3-yl) wherein said heterocycloalkyl is optionally substituted with $C_{1-6}$alkyl (e.g., methyl), for example, 1-methylpyrrolidin-3-yl, 1-methyl-pyrrolindin-2-yl, 1-methyl-pyrrolindin-2-yl-methyl or 1-methyl-pyrrolindin-3-yl-methyl);

(iv) $R_3$ is
1) -D-E-F wherein:
D is a single bond, $C_{1-6}$alkylene (e.g., methylene), or aryl$C_{1-6}$alkylene (e.g., benzylene or —$CH_2C_6H_4$—);
E is
a single bond,
$C_{1-4}$alkylene (e.g., methylene, ethynylene, prop-2-yn-1-ylene),
$C_{0-4}$alkylarylene (e.g., phenylene or —$C_6H_4$—, -benzylene- or —$CH_2C_6H_4$—), wherein the arylene group is optionally substituted with halo (e.g., Cl or F),
heteroarylene (e.g., pyridinylene or pyrimidinylene),
amino$C_{1-6}$alkylene (e.g., —$CH_2$N(H)—),
amino (e.g., —N(H)—);
$C_{3-8}$cycloalkylene optionally containing one or more heteroatom selected from N or O (e.g., piperidinylene),
F is
H,
halo (e.g., F, Br, Cl),
$C_{1-6}$alkyl (e.g., isopropyl or isobutyl),
halo$C_{1-6}$alkyl (e.g., trifluoromethyl),
aryl (e.g., phenyl),
$C_{3-8}$cycloalkyl optionally containing one or more atom selected from a group consisting of N, S or O (e.g., cyclopentyl, cyclohexyl, piperidinyl, pyrrolidinyl, tetrahydro-2H-pyran-4-yl, or morpholinyl), and optionally substituted with one or more $C_{1-6}$alkyl (e.g., methyl or isopropyl), for example, 1-methylpyrrolidin-2-yl, pyrrolidin-1-yl, pyrrolidin-2-yl, piperidin-2-yl, 1-methyl-piperidin-2-yl, 1-ethylpiperidin-2-yl,
heteroaryl (e.g., pyridyl (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl)), triazolyl (e.g., 1,2,4-triazol-1-yl), tetrazolyl (e.g., tetrazol-5-yl), alkyloxadiazolyl (e.g., 5-methyl-1,2,4-oxadiazol), wherein said heteroaryl is optionally substituted with one or more $C_{1-6}$alkyl, halo (e.g., fluoro) or halo$C_{1-6}$alkyl;
$C_{1-6}$alkoxy,
—O-halo$C_{1-6}$alkyl (e.g., —O—CF$_3$),
$C_{1-6}$alkylsulfonyl (for example, methylsulfonyl or —S(O)$_2$CH$_3$),
—C(O)—R$_{13}$, wherein R$_{13}$ is —N(R$_{14}$)(R$_{15}$), $C_{1-6}$alkyl (e.g., methyl), —OC$_{1-6}$alkyl (e.g., —OCH$_3$), halo$C_{1-6}$alkyl (trifluoromethyl), aryl (e.g., phenyl), or heteroaryl;
—N(R$_{14}$)(R$_{15}$);
or
2) a substituted heteroaryl$C_{1-6}$aklyl, e.g., substituted with halo$C_{1-6}$alkyl;
or
3) attached to one of the nitrogens on the pyrazolo portion of Formula I and is a moiety of Formula A

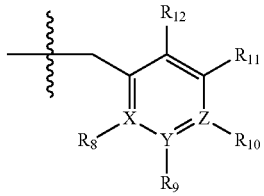

Formula A wherein:
X, Y and Z are, independently, N or C,
R$_8$, R$_9$, R$_{11}$ and R$_{12}$ are independently H or halogen (e.g., Cl or F); and
R$_{10}$ is
halogen (e.g., fluoro or chloro),
$C_{1-6}$alkyl,
$C_{3-8}$cycloalkyl,
hetero$C_{3-8}$cycloalkyl (e.g., pyrrolidinyl or piperidinyl),
halo$C_{1-6}$alkyl (e.g., trifluoromethyl),
aryl (e.g., phenyl) or heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkyloxadiazolyl (e.g., 5-methyl-1,2,4-oxadiazol), pyrazolyl (e.g., pyrazol-1-yl), wherein said aryl, heteroaryl, cycloalkyl or heterocycloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl),
$C_{1-6}$alkyl sulfonyl (e.g., methyl sulfonyl),
arylcarbonyl (e.g., benzoyl),
heteroarylcarbonyl,
$C_{1-6}$alkoxycarbonyl, (e.g., methoxycarbonyl),
Aminocarbonyl,
—N(R$_{14}$)(R$_{15}$);
preferably R$_{10}$ is phenyl, pyridyl, piperidinyl or pyrrolidinyl optionally substituted with the substituents previously defined, e.g. optionally substituted with halo or alkyl;
provided that when X, Y or X is nitrogen, R$_8$, R$_9$ or R$_{10}$, respectively, is not present;

(v) R$_4$ and R$_5$ are independently:
H,
$C_{1-6}$alkyl (e.g., methyl, isopropyl, isobutyl, n-propyl),
$C_{3-8}$cycloalkyl (e.g., cyclopentyl or cyclohexyl),
$C_{3-8}$heterocycloalkyl (e.g., pyrrolidinyl (for example pyrrolidin-3-yl or pyrrolidin-1-yl), piperidinyl (for example, piperidin-1-yl), morpholinyl),
—$C_{0-6}$alkylaryl (e.g., phenyl or benzyl) or
—$C_{0-6}$alkylheteroaryl (e.g., pyrid-4-yl, pyrid-2-yl or pyrazol-3-yl)
wherein said aryl or heteroaryl is optionally substituted with one or more halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl);
(vi) R$_6$ is H, $C_{1-6}$alkyl (e.g., methyl or ethyl) or $C_{3-8}$cycloalkyl;
(vii) R$_{14}$ and R$_{15}$ are independently H or $C_{1-6}$alkyl,
in free or salt form.

In one embodiment the invention provides that the PDE1 inhibitors for use in the methods of treatment and prophylaxis described herein are Formula X, e.g.:

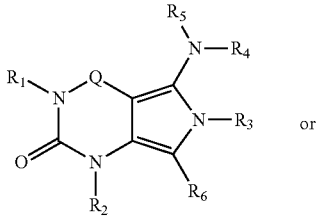

Formala XA or

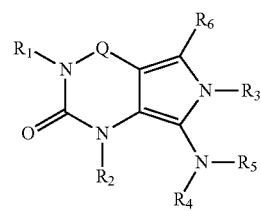

Formula XB

Formula X-A Formula X-B wherein
(i) Q is —C(=S)—, —C(=O)—, —C(=N(R$_7$))— or —C(R$_{14}$)(R$_{15}$)—;
(ii) R$_1$ is H or $C_{1-6}$alkyl (e.g., methyl or ethyl);
(iii) R$_2$ is H, $C_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, R$_2$ may be a trifluoromethyl or 2,2,2-trifluoroethyl, N(R$_{14}$)(R$_{15}$)— $C_{1-6}$alkyl (e.g., 2-(dimethylamino)ethyl or 2-aminopropyl), aryl$C_{1-6}$alkyl (e.g., phenyl or benzyl), heteroaryl$C_{1-6}$alkyl (e.g., pyridinylmethyl), $C_{1-6}$alkoxyaryl-$C_{1-6}$alkyl (e.g., 4-methoxybenzyl); -G-J wherein:
G is a single bond or, alkylene (e.g., methylene); J is cycloalkyl or heterocycloalkyl (e.g., oxetan-2-yl, pyrolyin-3-yl, pyrolyin-2-yl) optionally substituted with one or more $C_{1-6}$alkyl (e.g., (1-methylpyrolidin-2-yl)), amino (e.g., —NH$_2$), for example, -G-J may be —$C_{0-4}$alkyl-$C_{3-8}$cycloalkyl (e.g., cyclopentyl, cyclohexyl or cyclopropylmethyl) optionally substituted with one or more $C_{1-6}$alkyl, amino (e.g., —NH$_2$), for example, 2-aminocyclopentyl or 2-aminocyclohexyl, wherein said cycloalkyl optionally contains one or more heteroatom selected from N and O (e.g., pyrrolidinyl, for example, pyrrolidin-3-yl or pyrrolidin-2-yl, 1-methyl-pyrrolindin-2-yl, 1-methyl-pyrrolindin-3-yl, 1-methyl-pyrrolindin-2-yl-methyl or 1-methyl-pyrrolindin-3-yl-methyl);

(iv) $R_3$ is

1) -D-E-F wherein:

D is a single bond, $C_{1-6}$alkylene (e.g., methylene), or arylalkylene (e.g., p-benzylene or —$CH_2C_6H_4$—);

E is a single bond, $C_{1-6}$alkylene (e.g., methylene) $C_{2-6}$alkynylene (e.g., ethynylene, prop-2-yn-1-ylene), ethynylene, prop-2-yn-1-ylene), —$C_{0-4}$alkylarylene (e.g., phenylene or —$C_6H_4$—, -benzylene- or —$CH_2C_6H_4$—), wherein the arylene group is optionally substituted with halo (e.g., Cl or F), heteroarylene (e.g., pyridinylene or pyrimidinylene), amino$C_{1-6}$alkylene (e.g., —$CH_2N$(H)—), amino (e.g., —N(H)—);

$C_{3-8}$cycloalkylene optionally containing one or more heteroatom selected from N or O (e.g., piperidinylene), F is

H, halo (e.g., F, Br, Cl), $C_{1-6}$alkyl (e.g., isopropyl or isobutyl), halo$C_{1-6}$alkyl (e.g., trifluoromethyl), aryl (e.g., phenyl), $C_{3-8}$cycloalkyl optionally containing at least one atom selected from a group consisting of N or O (e.g., cyclopentyl, N cyclohexyl, piperidinyl, pyrrolidinyl, tetrahydro-2H-pyran-4-yl, or morpholinyl), said cycloalkyl is optionally substituted with $C_{1-6}$alkyl (e.g., methyl or isopropyl), for example, 1-methyl-pyrrolidin-2-yl, pyrrolidin-1-yl, pyrrolidin-2-yl, piperidin-2-yl, 1-methyrpiperidin-2-yl, 1-ethylpiperidin-2-yl, heteroaryl optionally substituted with $C_{1-6}$alkyl, (e.g., pyridyl, (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), wherein said heteroaryl is optionally substituted with halo (e.g., fluoro) or halo$C_{1-6}$alkyl, for example, 6-fluoropyrid-2-yl; amino (e.g., —$NH_2$), $C_{1-6}$alkoxy, —O—halo$C_{1-6}$alkyl (e.g., -0-$CF_3$), $C_{1-6}$alkylsulfonyl (for example, methylsulfonyl or —$S(O)_2CH_3$),

—C(O)—$R_{13}$,

—N($R_{14}$)($R_{15}$); or 2) a substituted heteroarylaklyl, e.g., substituted with haloalkyl; or 3) attached to the nitrogen on the pyrrolo portion of Formula I and is a moiety of Formula A

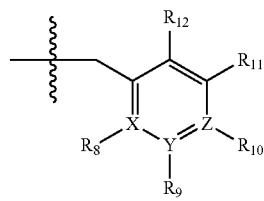

Formula A wherein X, Y and Z are, independently, N or C, and $R_8$, $R_9$, $R_{11}$ and $R_{12}$ are independently H or halogen (e.g., Cl or F); and $R_{10}$ is halogen, $C_{1-6}$alkyl, $C_{1-6}$alkoxy (e.g., methoxy), $C_{3-8}$cycloalkyl, hetero$C_{3-8}$cycloalkyl (e.g., pyrrolidinyl) halo$C_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl (e.g., imidazolyl or pyrazolyl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), $C_{1-6}$alkyl sulfonyl (e.g., methyl sulfonyl), arylcarbonyl (e.g., benzoyl), heteroarylcarbonyl, alkoxycarbonyl, (e.g., methoxycarbonyl), aminocarbonyl; wherein the aryl, heteroaryl, cycloalkyl or heterocycloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl) preferably $R_{10}$ is phenyl or pyridyl, e.g., 2-pyridyl optionally substituted with the substituents previously defined;

provided that when X, Y or X is nitrogen, $R_8$, $R_9$ or $R_{10}$, respectively, is not present; (v) $R_4$ and $R_5$ are independently H, $C_{1-6}$alkyl (e.g., methyl, isopropyl), $C_{3-8}$cycloalkyl (e.g., cyclopentyl), $C_{3-8}$heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl);

(vi) $R_6$ is H, $C_{1-6}$alkyl (e.g., methyl), hydroxy, $C_{1-6}$alkoxy, aryloxy, —N($R_{16}$)($R_{17}$), oxo (e.g., =O), or $C_{3-8}$Cycloalkyl;

(vii) $R_7$ is H, $C_{1-6}$alkyl (e.g., methyl) or $C_{3-8}$cycloalkyl wherein said cycloalkyl is optionally substituted with one or more oxo (e.g., 2,5-dioxopyrrolidin-1-yl);

(viii) $R_{13}$ is —N($R_{14}$)($R_{15}$), $C_{1-6}$alkyl (e.g., methyl), —O$C_{1-6}$alkyl (e.g., —$OCH_3$), halo$C_{1-6}$alkyl (trifluoromethyl), aryl (e.g., phenyl), or heteroaryl; and (ix) $R_{14}$ and $R_{15}$ are independently H or $C_{1-6}$alkyl;

(x) $R_{16}$ and $R_{17}$ are independently H, $C_{1-6}$alkyl, aryl (e.g., phenyl), heteroaryl, wherein said aryl or heteroaryl is optionally substituted with halo (e.g., fluoro), $C_{1-6}$alkoxy (e.g., methoxy); in free or salt form.

In one embodiment the invention provides that the PDE1 inhibitors for use in the methods of treatment and prophylaxis described herein are Formula XI:

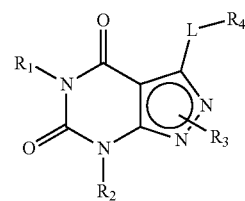

Formula XI wherein (i) L is S, SO or $SO_2$;

(ii) $R_2$ is H or $C_{1-6}$alkyl (e.g., methyl or ethyl);

(iii) $R_3$ is

H, $C_{1-6}$alkyl (e.g., isopropyl, isobutyl, neopentyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), —$C_{0-4}$alkyl-$C_{3-8}$cycloalkyl (e.g., cyclopentyl, cyclohexyl) optionally substituted with one or more amino (e.g., —$NH_2$), for example, 2-aminocyclopentyl or 2-aminocyclohexyl), wherein said cycloalkyl optionally contains one or more heteroatom selected from N and O and is optionally substituted with $C_{1-6}$alkyl (e.g., 1-methyl-pyrrolindin-2-yl, 1-methyl-pyrrolindin-3-yl, 1-methyl-pyrrolindin-2-yl-methyl or 1-methyl-pyrrolindin-3-yl-methyl), $C_{3-8}$heterocycloalkyl (e.g., pyrrolidinyl, for example, pyrrolidin-3-yl) optionally substituted with $C_{1-6}$alkyl (e.g., methyl), for example, 1-methylpyrrolidin-3-yl, $C_{3-8}$cycloalkyl-$C_{1-6}$alkyl (e.g., cyclopropylmethyl), halo$C_{1-6}$ alkyl (e.g., trifluoromethyl, 2,2,2-trifluoroethyl), —N($R_{14}$)($R_{15}$)—$C_{1-6}$alkyl (e.g., 2-(dimethylamino)ethyl, 2-aminopropyl), hydroxy$C_{1-6}$alkyl (e.g., (e.g., 3-hydroxy-2-methylpropyl, 1-hydroxyprop-2-yl), aryl$C_{0-6}$alkyl (e.g., benzyl), heteroaryl$C_{1-6}$alkyl (e.g., pyridinylmethyl), $C_{1-6}$alkoxyaryl$C_{1-6}$alkyl (e.g., 4-methoxybenzyl); -G-J wherein: G is a single bond or, alkylene (e.g., methylene);

J is cycloalkyl or heterocycloalkyl (e.g., oxetan-2-yl, pyrolyin-3-yl, pyrolyin-2-yl) optionally substituted with $C_{1-6}$alkyl (e.g., (1-methylpyrolidin-2-yl));

(iv) $R_3$ is attached to one of the nitrogens on the pyrazolo portion of Formula I and is a moiety of Formula A

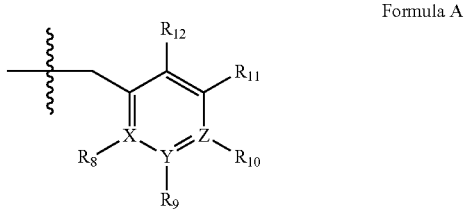

Formula A wherein X, Y and Z are, independently, N or C, and $R_8$, $R_9$, $R_{11}$ and $R_{12}$ are independently H or halogen (e.g., Cl or F); and $R_{10}$ is halogen, $C_{1-6}$alkyl, $C_{3-8}$cycloalkyl, hetero$C_{3-8}$cycloalkyl (e.g., pyrrolidinyl or piperidinyl) halo$C_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-15 yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-i-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl, pyridyl, e.g., 2-pyridyl, piperidinyl, or pyrrolidinyl; wherein the aryl, heteroaryl cycloalkyl or heterocycloalkyl is optionally substituted with one or more halo (e.g., F or Cl), $C_{1-6}$alkyl, $C_{1-6}$alkoxy, $C_{1-4}$haloalkyl (e.g., trifluoromethyl), and/or —SH, provided that when X, Y or X is nitrogen, $R_8$, $R_9$ or $R_{10}$, respectively, is not present; (v) $R_4$ is H, $C_{1-6}$alkyl (e.g., methyl, isopropyl), $C_{3-8}$cycloalkyl (e.g., cyclopentyl), $C_{3-8}$heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl); (vi) $R_{14}$ and $R_{15}$ are independently H or $C_{1-6}$alkyl, in free or salt form.

The invention further provides the use of PDE1 inhibitors of any of the preceding formulae (e.g., Formula I, II, III, IV, V, VI, VII, VIII, IX, X, XI), wherein the compound is selected from any of the following:

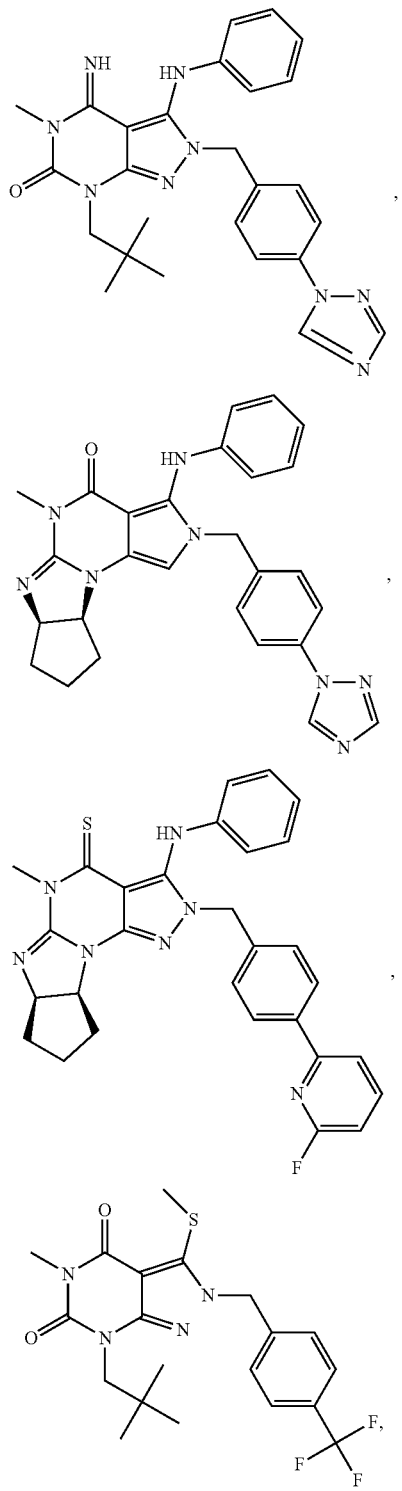

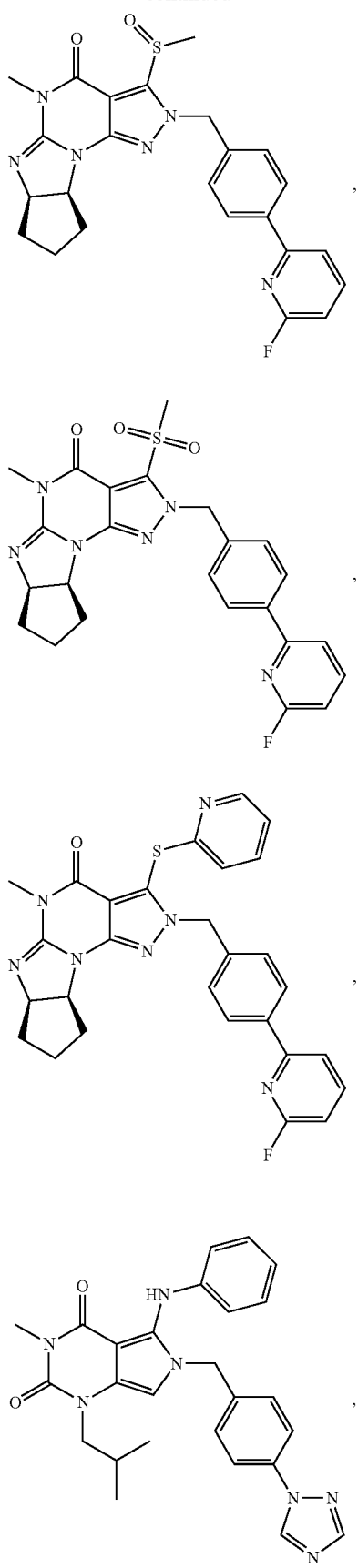 [SMILES: CN1C(=O)c2c(nn(Cc3ccc(-c4cccc(F)n4)cc3)c2S(C)=O)N2C1=N[C@@H]1CCC[C@@H]12 ; CN1C(=O)c2c(nn(Cc3ccc(-c4cccc(F)n4)cc3)c2S(C)(=O)=O)N2C1=N[C@@H]1CCC[C@@H]12 ; CN1C(=O)c2c(nn(Cc3ccc(-c4cccc(F)n4)cc3)c2Sc2ccccn2)N2C1=N[C@@H]1CCC[C@@H]12 ; CC(C)Cn1c(=O)n(C)c(=O)c2c(Nc3ccccc3)n(Cc3ccc(-n4cncn4)cc3)cc21]

In one embodiment, selective PDE1 inhibitors of the any of the preceding formulae (e.g., Formula I, II, III, IV, V, VI, VII, VIII, IX, X, XI) are compounds that inhibit phosphodiesterase-mediated (e.g., PDE1-mediated, especially PDE1A or PDE1C-mediated) hydrolysis of cGMP, e.g., the preferred compounds have an $IC_{50}$ of less than 1 μM, preferably less than 500 nM, preferably less than 50 nM, and preferably less than 5 nM in an immobilized-metal affinity particle reagent PDE assay, in free or salt form.

If not otherwise specified or clear from context, the following terms herein have the following meanings:

(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(c) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(d) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(f) For ease of reference, the atoms on the pyrazolo-pyrimidine core of the Compounds of the Invention are numbered in accordance with the numbering depicted in Formula I, unless otherwise noted.

(g) Wherein E is phenylene, the numbering is as follows:

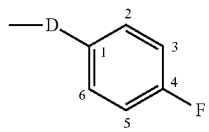

(h) It is intended that wherein the substituents end in "ene", for example, alkylene, phenylene or arylalkylene, said substitutents are intended to bridge or be connected to two other substituents. Therefore, methylene is intended to be —$CH_2$— and phenylene intended to be —$C_6H_4$— and arylalkylene is intended to be —$C_6H_4$—$CH_2$— or —$CH_2$—$C_6H_4$—.

(i) The Compounds of the Invention are intended to be numbered as follows:

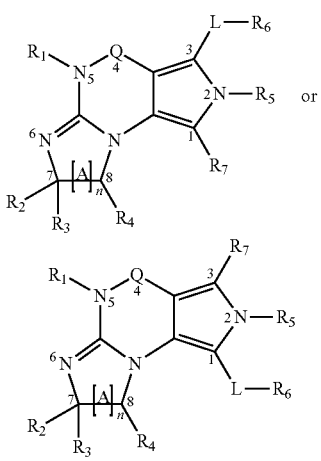

Compounds of the Invention, e.g., substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., Compounds of Formula I (Formula I-A and I-B), or a Compound of Formula II (e.g., II-A or II-B), may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention, encompassing any of the compounds disclosed herein, e.g., optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., Compounds of Formula III, or Compound of Formula IV as described herein, may exist in free or salt form, e.g., as acid addition salts.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a Compound of the Invention, in free or pharmaceutically acceptable salt form, in admixture with a pharmaceutically acceptable carrier.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a Compound of the Invention, in free, pharmaceutically acceptable salt or prodrug form, in admixture with a pharmaceutically acceptable carrier.

Methods of Making Compounds of the Invention

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various starting materials and/or Compounds of the Invention may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138. All references cited herein are hereby incorporated by reference in their entirety.

The Compounds of the Invention include their enantiomers, diastereoisomers and racemates, as well as their polymorphs, hydrates, solvates and complexes. Some individual compounds within the scope of this invention may contain double bonds.

Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and Abbreviations:
BuLi=n-butyllithium
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
LDA=lithium diisopropylamide
MeOH=methanol,
NBS=N-bromosuccinimide
NCS=N-chlorosuccinimide
NaHCO$_3$=sodium bicarbonate,
NH$_4$OH=ammonium hydroxide,
Pd$_2$(dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
TFMSA=trifluoromethanesulfonic acid
THF=tetrahedrofuran.

Methods of Using Compounds of the Invention

The Compounds of the Invention are useful in the treatment of diseases characterized by disruption of or damage to cGMP/PKG mediated pathways, e.g., as a result of increased expression of PDE1 or decreased expression of cGMP/PKG activity due to inhibition or reduced levels of inducers of cyclic nucleotide synthesis, such as dopamine and nitric oxide (NO). It is believed that by inhibiting PDE1A, for example, that this action could reverse or prevent the attenuation of cGMP/PKG signaling (e.g., enhance cGMP) and that this action could modulate cardiac hypertrophy. Therefore, administration or use of a preferred PDE1 inhibitor as described herein, e.g., a PDE1 inhibitor as hereinbefore described, e.g., a Compound of Formula Ia, Ib, IIa, IIb, III, IV, V, VI, VII, VIII, IX, X, XI, could provide a potential means to regulate cardiac hypertrophy (e.g., prevent and/or reverse cardiac hypertrophy), and in certain embodiments provide a treatment for various cardiovascular diseases and disorders.

A selective PDE1 inhibitor of the present invention, (e.g., of Formula Ia, Ib, IIa, IIb, III, IV, V, VI, VII, VIII, IX, X, XI), exhibit good oral availability in plasma with very minimal brain penetration in mice. Preferably, the half-life of the compounds is less than 2 hours. Preferably the Tmax is less than 1 hour. The blood/plasma ratio in mice administered the selective PDE1 inhibitor of the present invention is preferably less than 0.20.

Diseases and disorders that may be prevented or ameliorated by the enhancement of cGMP/PKG signaling (e.g., cardiovascular disease), e.g., using a Compound of Formula Ia, Ib, IIa, IIb, III, IV, V, VI, VII, VIII, IX, X, XI, include, but are not limited to: angina, stroke, renal failure, essential hypertension, pulmonary hypertension, secondary hypertension, isolated systolic hypertension, hypertension associated with diabetes, hypertension associated with atherosclerosis, renovascular hypertension, congestive heart failure, myocardial, angina, stroke and renal failure, hypertension, an inflammatory disease or disorder, fibrosis, cardiac hypertrophy, vascular remodeling, and an connective tissue disease or disorder (e.g., Marfan Syndrome).

In one embodiment the compounds of the invention as described herein (e.g., a Compound of Formula Ia, Ib, IIa, IIb, III, IV, V, VI, VII, VIII, IX, X, XI) are useful in the treatment or prevention of stroke by treating or preventing transient ischemic attacks (TIA). Without being bound by any theory, it is believed that the compounds may prevent or treat the risk of transient ischemic attacks by actually increasing the amount and/or concentration of blood flow to the brain. It is contemplated that the compounds as described herein could increase the blood flow to the brain without significant passage across the blood brain barrier.

In another embodiment, the invention further provides using the compounds of the invention (e.g., a Compound of Formula Ia, Ib, IIa, IIb, III, IV, V, VI, VII, VIII, IX, X, XI) for treatment of disease and disorders as follows: Duchenne muscular dystrophy, Becker muscular dystrophy, limb-girdle muscular dystrophy, myotonic dystrophy, and Emery-Dreifuss muscular dystrophy. In one embodiment, the compounds of the present invention are useful in treating cardiac dysfunction associated with aforementioned types of muscular dystrophy. In one embodiment the compounds as described herein may potentially reduce or reverse the cardiac hypertrophy that may be associated with these aforementioned types of muscular dystrophy.

"PDE1 inhibitor" as used herein describes a compound(s) which selectively inhibit phosphodiesterase-mediated (e.g., PDE1-mediated, especially PDE1B-mediated) hydrolysis of cGMP, e.g., with an $IC_{50}$ of less than 1 µM, preferably less than 750 nM, more preferably less than 500 nM, more preferably less than 50 nM in an immobilized-metal affinity particle reagent PDE assay.

The phrase "Compounds of the Invention" or "PDE 1 inhibitors of the Invention", or like terms, encompasses any and all of the compounds disclosed herewith, e.g., a Compound of Formula I, Formula II, Formula III, Formula IV, Formula V, Formula VI, Formula VII, Formula VIII, Formula IX, Formula X, or Formula XI.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat a specific disease or disorder.

The term "pulmonary hypertension" is intended to encompass pulmonary arterial hypertension.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention, e.g., Formula I, II, III, IV, V, VI, VII, VIII, IX, X, and XI as hereinbefore described, in free or pharmaceutically acceptable salt form, may be used as a sole therapeutic agent, but may also be used in combination or for co-administration with other active agents.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1

Measurement of PDEIB Inhibition In Vitro Using IMAP Phosphodiesterase Assay Kit

Phosphodiesterase I B (PDEIB) is a calcium/calmodulin dependent phosphodiesterase enzyme that converts cyclic guanosine monophosphate (cGMP) to 5'-guanosine monophosphate (5'-GMP). PDEIB can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Amp). Inhibition of phosphodiesterase, therefore, is detected as a decrease in Amp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: The following phosphodiesterase enzymes may be used: 3',5'-cyclic-nucleotide-specific bovine brain phosphodiesterase (Sigma, St. Louis, Mo.) (predominantly PDEIB) and recombinant full length human PDE1 A and PDE1B (r-hPDE1 A and r-hPDE1B respectively) which may be produced e.g., in HEK or SF9 cells by one skilled in the art. The PDE1 enzyme is reconstituted with 50% glycerol to 2.5 U/ml. One unit of enzyme will hydrolyze 1.0 μm of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), IOmM Tris-HCl pH 7.2, IOmM $MgCl_2$, 0.1% BSA, 0.05% $NaN_3$) to yield a final concentration of 1.25 mU/ml. 99 μℓ of diluted enzyme solution is added into each well in a flat bottom 96-well polystyrene plate to which 1 μℓ of test compound dissolved in 100% DMSO is added. The compounds are mixed and pre-incubated with the enzyme for 10 min at room temperature. The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μℓ of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Amp).

A decrease in GMP concentration, measured as decreased Amp, is indicative of inhibition of PDE activity. IC50 values are determined by measuring enzyme activity in the presence of 8 to 16 concentrations of compound ranging from 0.0037 nM to 80,000 nM and then plotting drug concentration versus AmP, which allows IC50 values to be estimated using nonlinear regression software (XLFit; IDBS, Cambridge, Mass.).

The Compounds of the Invention are tested in an assay as described or similarly described herein for PDE1 inhibitory activity.

Example 2

Inhibition of Cardiac Hypertrophy

A selective PDE1 inhibitor of the present invention is tested in a mouse model where the mice are treated with isoproterenol. Such a model can be useful for extrapolating to diseases or disorders involving an enlargement of the heart or cardiac tissue, e.g., congestive heart disease.

Isoproterenol treatment in mice increases cardiac size in mice untreated with a selective PDE1 inhibitor of the present invention. Size is indicated by heart weight (g)/tibia length (mm). At 3 mg/kg, administration of the selective PDE1 inhibitor of the present invention significantly decreases cardiac hypertrophy in mice which are treated with isoproterenol. A selective PDE1 inhibitor of the present Invention also significantly prevent cardiac hypertrophy at administration of 10 mg/kg.

Example 3

Cellular Screening Systems

Primary Human Cardiomyocytes

Primary human cardiomyocytes have a unique signaling system involving a synergy of calcium and cAMP to achieve proper force of contraction. cGMP is an important moderator of cell function that prevents hypertrophic responses that are the mark of Heart Disease, and PDE1C is abundant in these cells.

A selective PDE1 inhibitor of the present invention elevates cGMP in Human Cardiomyocytes in Culture. When measured in conjunction with Sildenafil, the selective PDE1 inhibitor is about 100-fold more potent than Sildenafil in enhancing cGMP. Such potency would have various application in various cardiovascular applications.

Primary Human Smooth Muscle Cells

Primary human smooth muscle cells contain PDE1C as well as PDE3, 4 and. Consequently, primary human smooth muscle cell may be important mediators of the pathology in Heart Disease.

Atrial natriuretic peptide (ANP) is a peptide which binds the natriuretic peptide receptor-A (NPRA) and which may trigger activation of its guanylyl cyclase domain increasing cGMP production. Following a 30-minute pretreatment with a selective PDE1 inhibitor of the present invention there is an increase in ANP response in vascular aortic smooth muscle (VASM) Cells.

Neutrophils

During heart disease progression, part of the inflammatory component of Heart Disease PDE1B may be up-regulated during the process of differentiation from Neutrophils to Macrophages.

Immortalized Human Neutrophil Line (HL60 Cells) are used to study the Macrophage differentiation (inflammatory) process. In HL60 macrophages, at about 100 nM, a selective PDE1 inhibitor of the present invention amplifies the effect of Atrial Natriuretic Peptide (ANF), wherein cGMP production increases as compared to cells where a selective PDE1 inhibitor is not used in combination with ANF.

Example 4

Mdx Mouse Model

The mdx mouse model is used to understand muscle degeneration and regeneration in Duchenne Muscular Dystrophy.

The dystrophic mdx mouse has a point mutation within its dystrophin gene. This mutation has changed a codon representing glutamine amino acid to one representing thymine amino acid. This single amino acid change causes the cell's machinery to stop; when this happens, the synthesis of dystrophin stops prematurely (known as premature stop codon). As a result, the mouse has no functional dystrophin in its muscles.

In conjunction with chronic dosing, a selective PDE1 inhibitor of the present invention demonstrates a cardioprotective effect in an mdx Mouse Model of diastolic heart failure.

What is claimed is:

1. A method of treatment or prophylaxis of a condition which may be ameliorated by modulating cGMP/PKG-dependent signaling pathways comprising administration of a PDE1 inhibitor to a patient in need thereof, wherein the disease or disorder is selected from the group consisting of: cardiovascular disease, angina, stroke, renal failure, essential hypertension, pulmonary hypertension, secondary hypertension, isolated systolic hypertension, hypertension associated with diabetes, hypertension associated with atherosclerosis, renovascular hypertension, congestive heart failure, myocardial infarction, an inflammatory disease or disorder, Duchenne muscular dystrophy, Becker muscular dystrophy, limb-girdle muscular dystrophy, myotonic dystrophy, Emery-Dreifuss muscular dystrophy and a connective tissue disease or disorder, wherein the PDE1 inhibitor is a compound of Formula V:

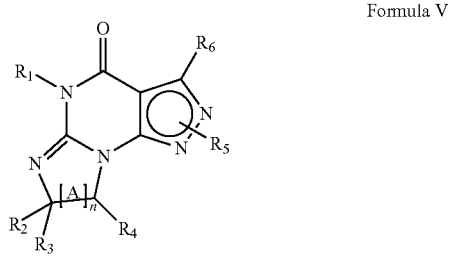

Formula V wherein
(i) $R_1$ is H or $C_{1-4}$ alkyl;
(ii) $R_4$ is H or $C_{1-4}$ alkyl and $R_2$ and $R_3$ are, independently, H or $C_{1-4}$ alkyl, aryl, heteroaryl, (optionally hetero)arylalkoxy, or (optionally hetero)arylalkyl;
or
$R_2$ is H and $R_3$ and $R_4$ together form a di-, tri- or tetramethylene bridge;
(iii) $R_5$ is a substituted heteroarylalkyl or
$R_5$ is attached to one of the nitrogens on the pyrazolo portion of Formula V and is a moiety of Formula A

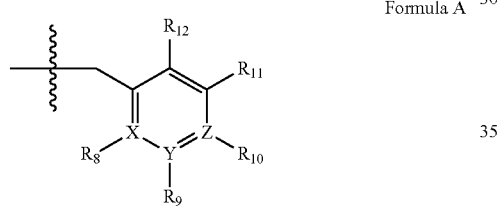

Formula A wherein X, Y and Z are, independently, N or C, and $R_8$, $R_9$, $R_{11}$ and $R_{12}$ are independently H or halogen, and $R_{10}$ is halogen, alkyl, cycloalkyl, haloalkyl, aryl, heteroaryl, or thiadiazolyl, diazolyl, triazolyl, tetrazolyl, arylcarbonyl, alkylsulfonyl, heteroarylcarbonyl, or alkoxycarbonyl; provided that when X, Y, or Z is nitrogen, $R_8$, $R_9$, or $R_{10}$, respectively, is not present; and
(iv) $R_6$ is H, alkyl, aryl, heteroaryl, arylalkyl, arylamino, hetarylamino, N,N-dialkylamino, N,N-diarylamino, or N-aryl-N-(arylakyl)amino; and
(v) n=0 or 1;
(vi) when n=1, A is —C($R_{13}R_{14}$)—
wherein $R_{13}$ and $R_{14}$, are, independently, H or $C_{1-4}$ alkyl, aryl, heteroaryl, (optionally hetero)arylalkoxy or (optionally hetero)arylalkyl;
wherein aryl is optionally substituted with $C_{1-4}$ alkyl, halogen, halo $C_{1-4}$alkyl, hydroxyl or $C_{1-4}$carboxy or an additional aryl or heteroaryl; or
heteroaryl or thiadiazolyl is optionally substituted with $C_{1-4}$alkyl, halogen, halo$C_{1-4}$alkyl, hydroxyl or $C_{1-4}$ carboxy;
in free or pharmaceutically acceptable salt form.

2. The method of claim 1, wherein the compound inhibits phosphodiesterase mediated hydrolysis of cGMP/PKG and wherein inhibition of phosphodiesterase prevents or treats cardiac hypertrophy.

3. The method of claim 1, wherein the PDE1 inhibitor is a PDE1A or PDE1C inhibitor.

4. The method of claim 1, wherein the PDE1 inhibitor is a PDE1B inhibitor.

5. The method claim 1, wherein the PDE1 inhibitor is administered in order to treat or prevent a cardiovascular disease or disorder.

6. The method of claim 1, wherein the disease is selected from the group consisting of: Duchenne muscular dystrophy, Becker muscular dystrophy, limb-girdle muscular dystrophy, myotonic dystrophy, and Emery-Dreifuss muscular dystrophy.

7. The method of claim 1, wherein the disease or disorder is a stroke.

8. The method of claim 7, wherein the stroke is characterized as a transient ischemic attack.

9. The method of claim 1, wherein the PDE1 inhibitor is administered to prevent or treat cardiac hypertrophy.

10. The method of claim 1, wherein a PDE1 inhibitor is administered in combination with a PDE5 inhibitor.

11. The method of claim 1, wherein the PDE1 inhibitor is selected from the group of consisting of:

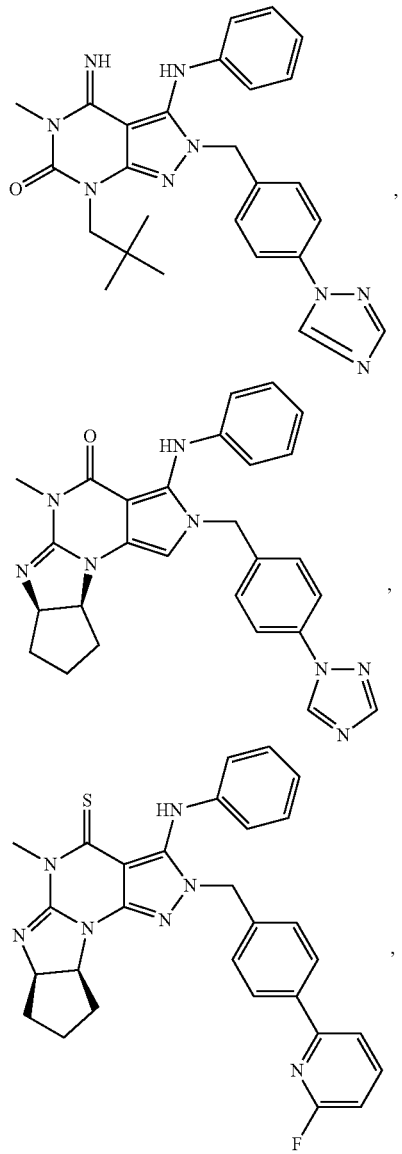

-continued
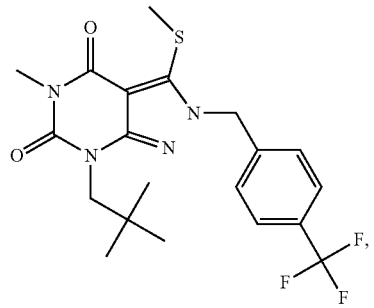
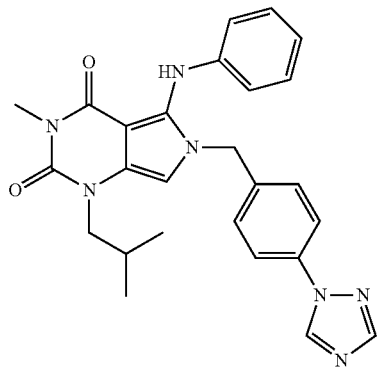
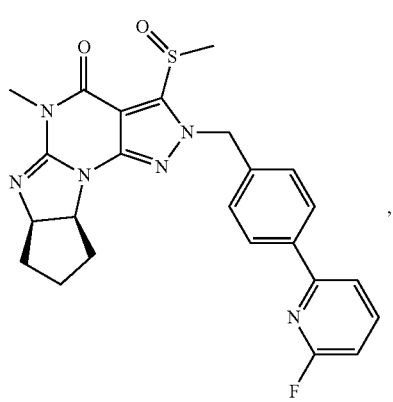
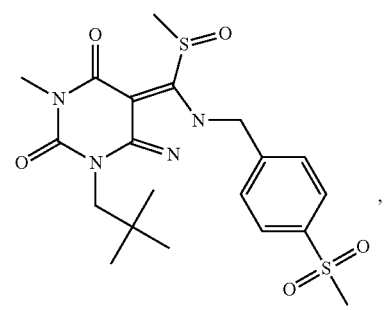
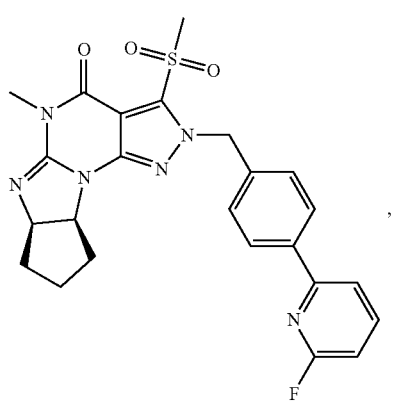
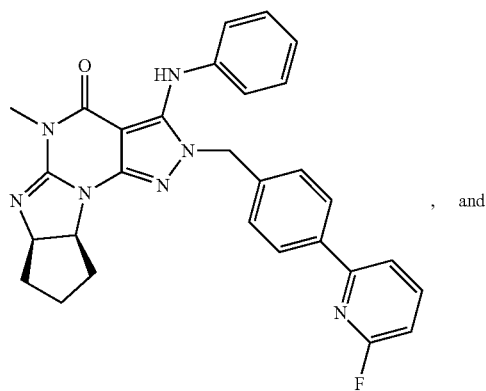, and
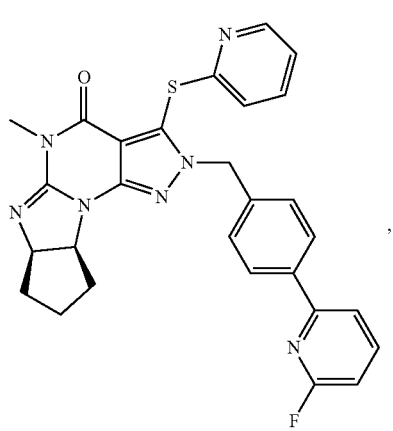
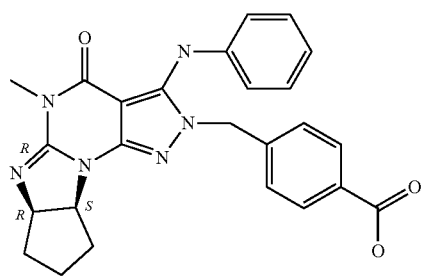
in free or pharmaceutically acceptable salt form.
12. The method of claim 1, wherein the disease or disorder is renal failure.
13. The method of claim 1, wherein the PDE1 inhibitor is selected from the group of consisting of:

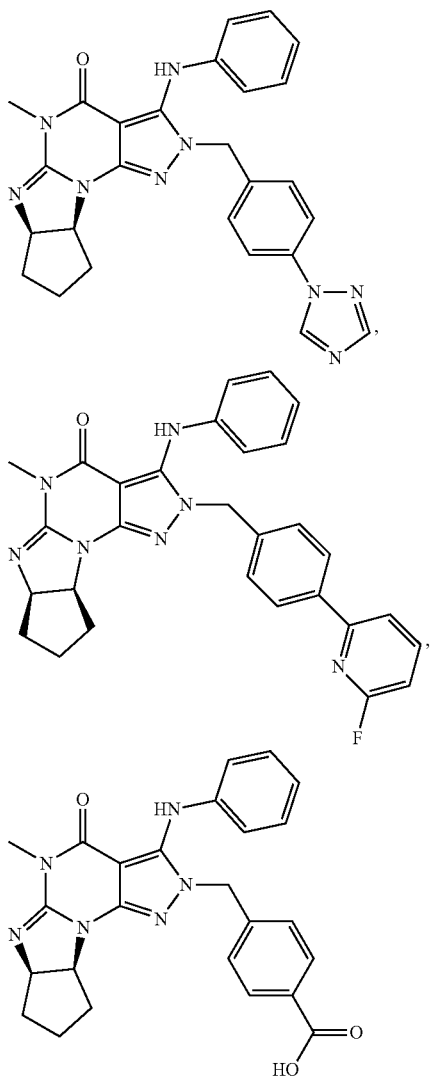

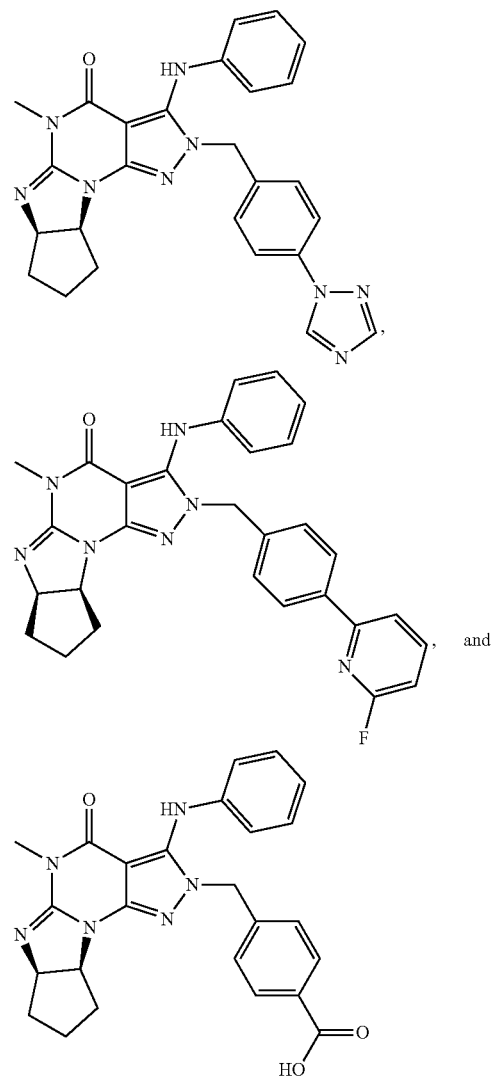

in free or pharmaceutically acceptable salt form.

14. The method of claim 1, wherein the PDE1 inhibitor is the following compound:

in free or pharmaceutically acceptable salt form.

16. The method of claim 12, wherein the PDE1 inhibitor is the following compound:

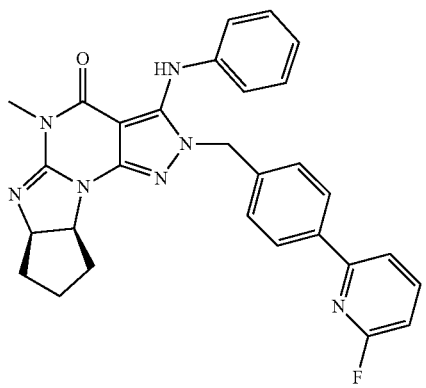 [SMILES: CN1C(=O)c2c(nn(Cc3ccc(-c4cccc(F)n4)cc3)c2Nc2ccccc2)N2C1=N[C@@H]1CCC[C@@H]12]

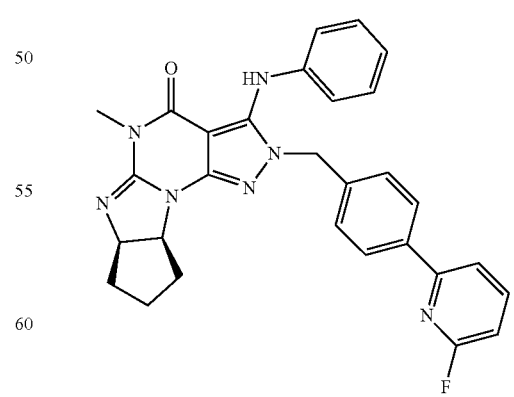

in free or pharmaceutically acceptable salt form.

15. The method of claim 12, wherein the PDE1 inhibitor is selected from the group of consisting of:

in free or pharmaceutically acceptable salt form.

* * * * *